United States Patent
Karo et al.

(10) Patent No.: US 7,611,469 B2
(45) Date of Patent: Nov. 3, 2009

(54) CUFF FOR BLOOD PRESSURE MONITOR, BLOOD PRESSURE MONITOR, LIVING BODY PRESSING APPARATUS, AND LIVING BODY INFORMATION MEASURING APPARATUS

(75) Inventors: Hiromichi Karo, Kyoto (JP); Yoshihiko Sano, Kyoto (JP); Hiroshi Kishimoto, Kyoto (JP); Yoshinori Tsurumi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 392 days.

(21) Appl. No.: 11/303,946

(22) Filed: Dec. 19, 2005

(65) Prior Publication Data
US 2006/0135872 A1    Jun. 22, 2006

(30) Foreign Application Priority Data
Dec. 20, 2004    (JP)    ............................. 2004-368140

(51) Int. Cl.
*A61B 5/02*    (2006.01)
*A61B 17/00*   (2006.01)
(52) U.S. Cl. .................. 600/499; 600/490; 606/202
(58) Field of Classification Search ............... 600/490, 600/493–496, 500; 606/202, 203
See application file for complete search history.

(56) References Cited

U.S. PATENT DOCUMENTS 5,243,991 A  *  9/1993  Marks ...................... 600/499

2002/0170359 A1  11/2002  Yamakoshi et al.

FOREIGN PATENT DOCUMENTS

| CN | 1308918 A | 8/2001 |
|---|---|---|
| CN | 1383783 A | 12/2002 |
| EP | 1 075 846 | 2/2001 |
| EP | 1-125-551 A2 | 8/2001 |
| EP | 1-374-762 A1 | 1/2004 |
| JP | 02-107226 | 4/1990 |
| JP | 09-117419 A | 5/1997 |
| JP | 11-299746 A | 11/1999 |
| JP | 2001-224558 | 8/2001 |
| RU | 2 231 967 | 7/2004 |
| SU | 1618385 | 1/1991 |
| WO | WO-99/55400 | 11/1999 |

OTHER PUBLICATIONS

Chinese Office Action dated Jun. 1, 2007, directed to counterpart CN Application No. 200510137736.4, (11 pages).
Russian Notice of Allowance dated Jun. 19, 2007, directed to counterpart RU application No. 2005139792.

* cited by examiner

Primary Examiner—Charles A Marmor, II
Assistant Examiner—Christian Y Jang
(74) Attorney, Agent, or Firm—Morrison & Foerster LLP

(57) ABSTRACT

A cuff as a living body pressing apparatus provided for a blood pressure monitor as a living body information measuring apparatus includes an air bag and a curled elastic member wound annularly around an outer side of the air bag. The air bag has an engagement portion at each side end portion in the width direction. The engagement portion is folded along the end face of the curled elastic member toward the curled elastic member, and secured to the outer peripheral surface of the curled elastic member. With this configuration, it is possible to provide a living body pressing apparatus capable of preventing occurrence of lateral displacement, and a living body information measuring apparatus provided with the living body pressing apparatus.

9 Claims, 17 Drawing Sheets

CUFF FOR BLOOD PRESSURE MONITOR, BLOOD PRESSURE MONITOR, LIVING BODY PRESSING APPARATUS, AND LIVING BODY INFORMATION MEASURING APPARATUS

BACKGROUND OF THE INVENTION

1. Field of the Invention

The present invention relates to a living body pressing apparatus having a fluid bag, and a living body information measuring apparatus provided with the same. Particularly, the present invention relates to a cuff for a blood pressure monitor, and a blood pressure monitor provided with the same.

2. Description of the Background Art

A blood pressure monitor, a pulse wave detector and others are generally known as living body-information measuring apparatuses for measuring living body information. Normally, the blood pressure monitor and the pulse wave detector each include a living body pressing apparatus. In the state where the living body pressing apparatus is mounted on a measurement site of the living body, a fluid bag contained in the living body pressing apparatus is inflated to press the living body to measure the living body information.

For example, to measure a blood pressure value, a cuff provided with a fluid bag for pressing an artery located within a living body is wound around the body surface, and arterial pressure pulse waves caused in the artery by inflation/deflation of the fluid bag are detected to measure the blood pressure value. Here, the cuff refers to a band-shaped structure having a bladder, which can be wound around a part of a living body, for use in measurement of arterial pressure of an upper limb, a lower limb or the like by introducing fluid such as gas or liquid into the bladder. Thus, the cuff represents the concept including the fluid bag as well as members for winding the fluid bag around the living body. Particularly, the cuff wound around and fitted on a wrist or an upper arm is also called an arm band or a mancheffe.

Recently, blood pressure monitors are often used not only in medical treatment facilities such as hospitals but also in the households as an apparatus for checking the physical conditions day by day. As such, there are strong demands for improvement in handling of the blood pressure monitors, particularly for ease in fitting operation. To this end, downsizing of the cuff has been attempted. To downsize the cuff, it is necessary to narrow the cuff in the width direction (i.e., direction parallel to the axial direction of the measurement site (e.g., wrist, upper arm or the like) to which the cuff is applied).

To narrow the width of the cuff for the blood pressure monitor, it is important to ensure that the artery is sufficiently pressed for avascularization. In the case of using a cuff for a blood pressure monitor having a large width, a long length in the axial direction of the measurement site covered by the cuff can be guaranteed, which enables sufficient pressing and avascularization of the artery. However, if the width of the cuff is narrowed, the length in the axial direction of the measurement site covered by the cuff becomes short, in which case it would be difficult to sufficiently press the artery for avascularization.

A cuff for a blood pressure monitor disclosed in Japanese Patent Laying-Open No. 02-107226 and a cuff for a blood pressure monitor disclosed in Japanese Patent Laying-Open No. 2001-224558, for example, are known as those directed to prevent degradation of avascularization performance in association with a decreased cuff width. In each of the cuffs for a blood pressure monitor disclosed in these publications, an air bag identified as a fluid bag arranged inside the cuff is provided with a gusset at each side end portion in the width direction. When the air bag is inflated, the gussets expand to make the air bag inflated more uniformly in the width direction. With this configuration, it is possible to sufficiently press the artery for avascularization, not only at the central portion of the cuff, but also at and around the respective side end portions thereof. This ensures accurate measurement of the blood pressure value even if the cuff is narrowed in width.

When the gusset is provided at each side end portion in the width direction of the air bag, however, the side end portion in the width direction of the air bag increases in height in the thickness direction when the air bag is inflated. This may induce lateral displacement of the air bag as will be described below.

FIG. 23 is a schematic diagram showing the state where a typical wrist blood pressure monitor is mounted on a measurement site of the wrist. FIG. 24 is a schematic cross sectional view of the cuff for the blood pressure monitor shown in FIG. 23, taken along the line XXIV-XXIV in FIG. 23. FIG. 25 is a schematic diagram showing the state where there occurs lateral displacement of the cuff for the wrist blood pressure monitor in the measurement state shown in FIG. 23. FIG. 26 is a schematic cross sectional view of the cuff for a blood pressure monitor and the wrist shown in FIG. 25, taken along the line XXVI-XXVI in FIG. 25.

As shown in FIG. 23, the wrist blood pressure monitor 100 includes a main body 110 and a cuff 130. Upon measurement of blood pressure values using wrist blood pressure monitor 100, cuff 130 of blood pressure monitor 100 is wound around the wrist 300 as the measurement site in the circumferential direction. As shown in FIG. 24, cuff 130 primarily includes a cover member 140 in a bag shape, and an air bag 150 and a curled elastic member 160 arranged inside cover member 140. Curled elastic member 160 is elastic and curved to temporarily fit the cuff on the wrist. Cover member 140, air bag 150 and curled elastic member 160 extend with their longitudinal direction corresponding to the winding direction of cuff 130.

Cover member 140 is formed into a bag shape by laying an inner cover 141 made of highly elastic cloth or the like and an outer cover 142 made of less elastic cloth or the like one on the other and connecting their rims. Air bag 150 is formed into a bag shape by laying a resin sheet 151 constituting an inner wall portion located on the wrist side in the fitted state of the cuff and a resin sheet 152 constituting an outer wall portion located on the outer side than the inner wall portion one on the other and melting and bonding their rims, and has an inflated/deflated space 157 therein. Resin sheet 151 constituting the inner wall portion of air bag 150 has its side end portions folded and melted and bonded to resin sheet 152 constituting the outer wall portion, so that gussets are formed at the respective side wall portions of air bag 150. On the outer surface of the outer wall portion of air bag 150, curled elastic member 160 identified as an elastic member which is wound annularly and changeable in size in a radial direction, is attached using an attaching member such as a double-faced tape 171.

In wrist blood pressure monitor 100 of the above configuration, a pump, a valve and the like identified as an inflating/deflating portion arranged inside main body 110 are used to increase or decrease the pressure within inflated/deflated space 157 of air bag 150 arranged inside cuff 130 to inflate or deflate air bag 150. The blood pressure value is calculated based on the pressure information detected during inflation/deflation of air bag 150.

In the state where air bag 150 is inflated, if an external force is applied to outer cover 142 of cover member 140 in the direction parallel to the axial direction of wrist 300, the outer portion of cuff 130 may suffer lateral displacement in the axial direction of wrist 300, whereas the inner portion of cuff 130 will not suffer lateral displacement since it is in contact with wrist 300. This causes a part of cuff 130 to protrude as shown by a reference character 190 in FIG. 25. Even if there is no external force applied, pressure balance of air bag 150 may be lost due to the inclined shape of the surface of wrist 300, which may cause lateral displacement as well.

As shown in FIG. 26, the lateral displacement described above occurs as the pressure balance of air bag 150 is lost at the time of inflation, causing movement of curled elastic member 160, outer cover 142 and resin sheet 152 as a whole in the axial direction of wrist 300. When curled elastic member 160 moves in the axial direction of wrist 300, the air in air bag 150 moves toward the end portion of air bag 150 opposite to the moved direction of curled elastic member 160, which causes deformation of air bag 150, leading to occurrence of the protruding portion 190 described above. When such protruding portion 190 is generated, it is not possible to efficiently and uniformly press air bag 150 against wrist 300, in which case sufficient avascularization performance cannot be obtained, resulting in deterioration of measurement accuracy. Further, the both ends (regions A shown in FIG. 26) of the attached portion of air bag 150 and curled elastic member 160 would suffer a force in the direction causing peeling of air bag 150 from curled elastic member 160, which may degrade reliability of the attached portion.

The lateral displacement described above is more likely to occur as the thickness of inflated/deflated space 157 is greater with respect to the width of air bag 150 at the time of inflation. It poses a serious problem especially in the configuration where gussets are formed at both side end portions of air bag 150 for the purposes of preventing degradation of measurement accuracy attributable to reduction in width of cuff 130. The above problem however is not restricted to the cuff for a blood pressure monitor having such a configuration. A cuff for a blood pressure monitor not provided with the gussets at the side end portions of the air bag would also suffer the problem to some extent, for which a solution is sought.

Besides the blood pressure monitor, a pulse wave detector is also known as the living body information measuring apparatus provided with a fluid bag for use in pressing the living body. The pulse wave detector is an apparatus for measuring pulse waves by pressing a pressure-sensitive device as represented by a semiconductor sensor against a surface of the living body so as to measure pulse waves generated at an artery located relatively close to the skin of the living body. In the pulse wave detector as well, a fluid bag such as an air bag is used as a pressing member for pressing the pressure-sensitive surface of the sensor chip against the living body, which may cause a problem of lateral displacement similar to that of the cuff for a blood pressure monitor described above.

SUMMARY OF THE INVENTION

Generally, an object of the present invention is to provide a living body pressing apparatus having a fluid bag unlikely to cause lateral displacement and a living body information measuring apparatus provided with the same. Particularly, an object of the present invention is to provide a cuff for a blood pressure monitor capable of preventing occurrence of lateral displacement of the cuff, to thereby implement a highly reliable blood pressure monitor of high performance.

A cuff for a blood pressure monitor according to the present invention includes: a fluid bag inflated and deflated as a fluid comes in and out; and an elastic member wound annularly around an outer side of the fluid bag and changeable in size in a radial direction. The fluid bag has an inner wall portion located on an inner side when wound around a living body, an outer wall portion located on an outer side than the inner wall portion, and an engagement portion extending from a side end portion in a width direction of the fluid bag. The engagement portion is folded at the side end portion toward the elastic member, and secured in an immovable manner to a position on the side of the elastic member with respect to an outer surface of the outer wall portion.

In the cuff for a blood pressure monitor according to the present invention, it is preferable that the engagement portion is provided at least at one place in each side end portion in the width direction of the fluid bag.

In the cuff for a blood pressure monitor according to the present invention, it is preferable that the elastic member is formed of a plate-shaped member having an inner peripheral surface facing the fluid bag and an outer peripheral surface opposite to the inner peripheral surface, and the engagement portion is folded at the side end portion onto the outer peripheral surface of the elastic member and secured on the outer peripheral surface in an immovable manner.

In the cuff for a blood pressure monitor according to the present invention, it is preferable that the engagement portion is secured to the outer peripheral surface of the elastic member.

In the cuff for a blood pressure monitor according to the present invention, the engagement portions provided at the respective side end portions in the width direction of the fluid bag may be overlapped and secured to each other on the outer peripheral surface.

In the cuff for a blood pressure monitor according to the present invention, the fluid bag may be formed by laying a plurality of sheets one on another and joining their rims so that a space is formed therein. In this case, it is preferable that the engagement portion is formed by extending a rim of at least one of the sheets outwards.

In the cuff for a blood pressure monitor according to the present invention, it is preferable that the engagement portion is located approximately at a central portion in a longitudinal direction of the fluid bag.

A blood pressure monitor according to the present invention includes: any of the cuffs for a blood pressure monitor described above; an inflating/deflating portion for inflating and deflating the fluid bag; a pressure detecting portion for detecting a pressure in the fluid bag; and a blood pressure value calculating portion for calculating a blood pressure value based on pressure information detected by the pressure detecting portion.

A living body pressing apparatus according to the present invention includes: a fluid bag including a working face pressing a surface of a living body; and a base portion arranged along a main surface of the fluid bag located opposite to the working face. The fluid bag has an engagement portion extending from a side end portion of the fluid bag. The engagement portion is folded at the side end portion of the fluid bag toward the base portion, and secured in an immovable manner to a position on the side of the base portion with respect to the main surface of the fluid bag located opposite to the working face.

In the living body pressing apparatus according to the present invention, it is preferable that the base portion is formed of a plate-shaped member having a first main surface facing the fluid bag and a second main surface located opposite to the first main surface, and the engagement portion is folded at the side end portion of the fluid bag onto the second main surface of the base portion and engaged on the second main surface.

A living body information measuring apparatus according to a first aspect of the present invention is a kind of blood pressure monitor that includes: any of the living body pressing apparatuses described above; an inflating/deflating portion for inflating and deflating the fluid bag; a pressure detecting portion for detecting a pressure in the fluid bag; and a blood pressure value calculating portion for calculating a blood pressure value based on pressure information detected by the pressure detecting portion.

A living body information measuring apparatus according to a second aspect of the present invention is a kind of pulse wave detector that includes: any of the living body pressing apparatuses described above; a pressure-sensitive portion provided on the working face of the fluid bag; an inflating/deflating portion for inflating and deflating the fluid bag; and a pulse wave measuring portion for measuring a pulse wave based on pressure information detected by the pressure-sensitive portion.

According to the present invention, it is possible to provide a living body pressing apparatus unlikely to cause the lateral displacement as described above, and a living body information measuring apparatus provided with the same. Particularly, a cuff for a blood pressure monitor capable of preventing occurrence of the lateral displacement can be provided, ensuring uniform distribution of the pressing force over the measurement site. It is thus possible to implement a highly reliable blood pressure monitor of high performance.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention will be described in detail with reference to the drawings. In a first embodiment below, a wrist blood pressure monitor will be described as an example of a living body information measuring apparatus. In a second embodiment below, a pulse wave detector will be described as an example of the living body information measuring apparatus.

First Embodiment

Figure 1:
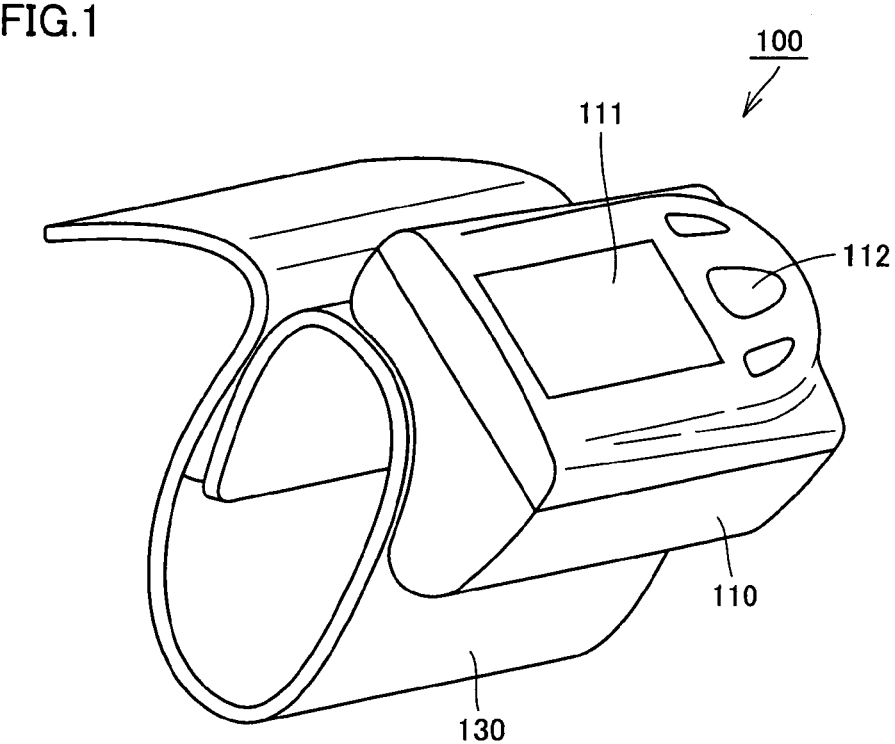
FIG. 1 is a perspective view of a blood pressure monitor according to a first embodiment of the present invention.

FIG. 1 is a perspective view of a blood pressure monitor according to the first embodiment of the present invention. As shown in FIG. 1, the blood pressure monitor 100 of the first embodiment of the present invention includes a main body 110 and a cuff 130. A display portion 111 and a manipulation portion 112 are arranged on the surface of main body 110. Cuff 130 is attached to main body 110.

Figure 2:
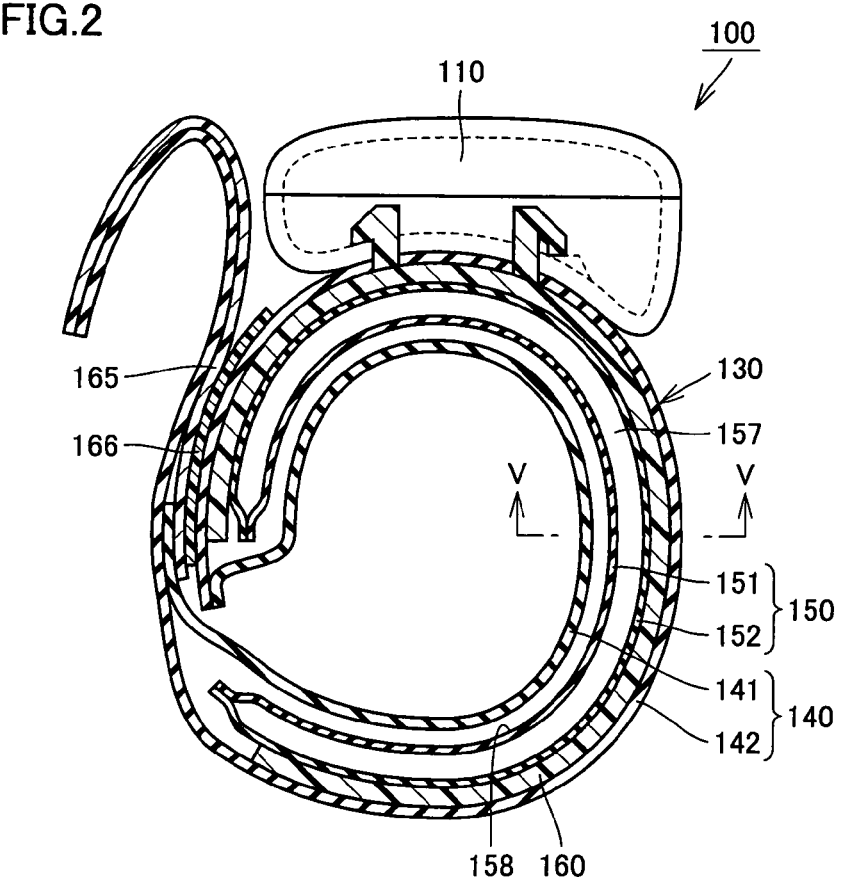
FIG. 2 is a vertical cross sectional view showing an inner structure of a cuff for the blood pressure monitor according to the first embodiment of the present invention.

FIG. 2 is a vertical cross sectional view showing an inner structure of the cuff for the blood pressure monitor shown in FIG. 1. As shown in FIG. 2, cuff 130 for the blood pressure monitor of the present embodiment primarily includes a cover member 140 of a bag shape that is made of highly elastic cloth or the like, an air bag 150 identified as a fluid bag that is arranged inside cover member 140, and a curled elastic member 160 that is arranged inside cover member 140 on an outer side of air bag 150 in the fitted state of the cuff. Cover member 140, air bag 150 and curled elastic member 160 extend with their longitudinal direction corresponding to the winding direction of cuff 130.

Cover member 140 has an inner cover 141 positioned on the inner side in the fitted state, and an outer cover 142 positioned on the outer side than inner cover 141. Inner cover 141 and outer cover 142 are laid one on the other and their rims are coupled to form a bag shape. On one end in the longitudinal direction of cover member 140, a velcro fastener 165 is provided on the inner peripheral surface. On the other end in the longitudinal direction of cover member 140, a velcro fastener 166 for engagement with velcro fastener 165 is attached to the outer peripheral surface. Velcro fasteners 165, 166 are members for securing blood pressure monitor 100 on the measurement site of the wrist in a stable manner when cuff 130 is mounted on the wrist.

Air bag 150 is made of a member of a bag shape that is formed using resin sheets. For example, in an air bag 150 contained in a cuff 130A for a blood pressure monitor according to Example 1 based on the present embodiment as will be described later, a resin sheet 151 constituting an inner wall portion located on the wrist side in the state where cuff 130A is wound around the wrist and a resin sheet 152 constituting an outer wall portion located on the outer side than the inner wall portion are laid one on the other and their rims are melted and bonded to form a bag shape, which has an inflated/deflated space 157 therein (for details, see Example 1 below). The surface on the wrist side of the inner wall portion of air bag 150 serves as a working face 158 for pressing the wrist. Inflated/deflated space 157 is connected via a tube 120 to an air system 121 for blood pressure measurement of main body 110, which will be described later (see FIG. 3).

As the material for the resin sheets constituting air bag 150, any material can be used as long as it exhibits excellent elasticity and prevents leakage of the air from inflated/deflated space 157 after melting and bonding. From these standpoints, optimal materials for the resin sheets include copolymer of ethylene-vinyl acetate (EVA), soft polyvinyl chloride (PVC), polyurethane (PU), crude rubber, and the like.

On the outer side of air bag 150, curled elastic member 160 identified as an elastic member is arranged, which is wound in an annular shape and elastically deformable in a radial direction. Curled elastic member 160 is attached to the outer surface of the outer wall portion of air bag 150 using an attaching member such as a double-faced tape (not shown). Curled elastic member 160 is configured to maintain its own annular shape corresponding to the contour of the wrist, and facilitates fitting of cuff 130 on the measurement site by the subject himself/herself Curled elastic member 160 is made of a resin member of polypropylene or the like, so as to exert sufficient elastic force.

Figure 3:
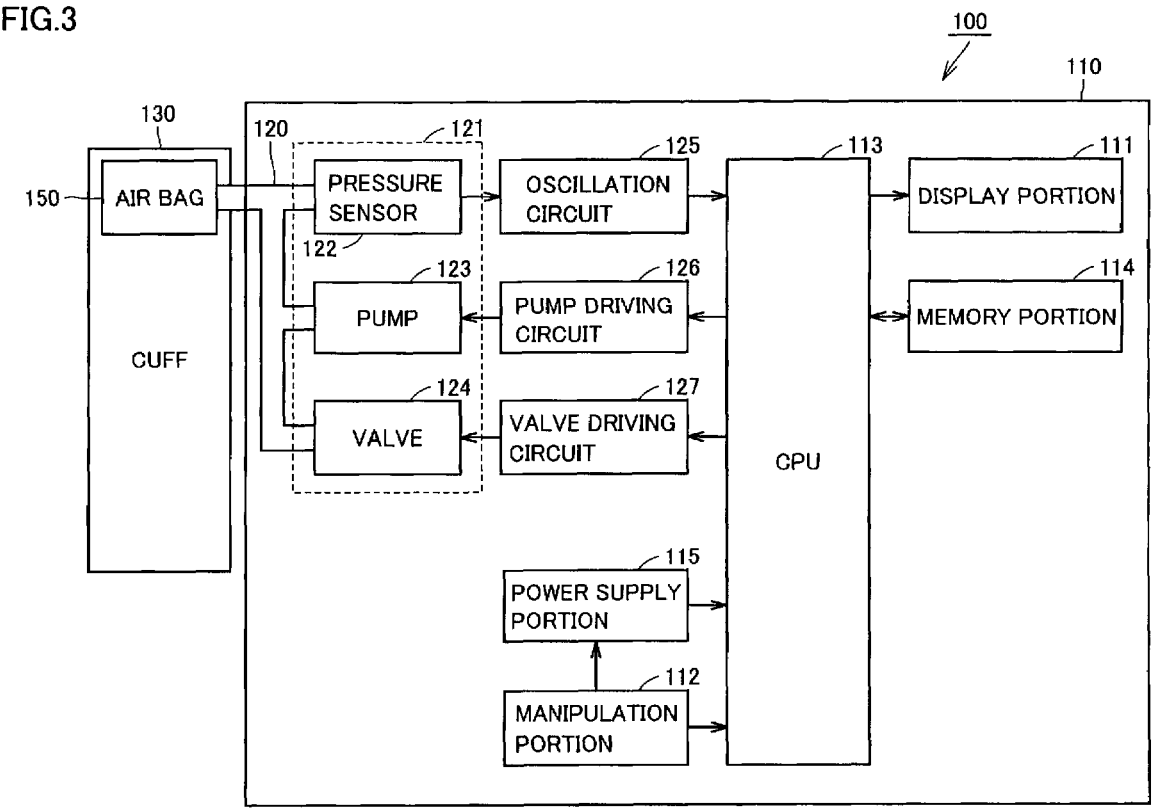
FIG. 3 is a block diagram showing a configuration of the blood pressure monitor according to the first embodiment of the present invention.

FIG. 3 is a block diagram showing a configuration of the blood pressure monitor according to the present embodiment. As shown in FIG. 3, main body 110 includes an air system 121 for blood pressure measurement for supplying and evacuating the air to and from air bag 150 via a tube 120, and an oscillation circuit 125, a pump driving circuit 126 and a valve driving circuit 127 which are provided in association with air system 121 for blood pressure measurement. These components function as an inflating/deflating portion for inflating and deflating air bag 150.

Main body 110 further includes a CPU (Central Processing Unit) 113 for controlling and monitoring the respective portions in a centralized manner, a memory portion 114 for storing a program for causing CPU 113 to conduct a prescribed operation and various information including blood pressure values measured, a display portion 111 for displaying the information including a blood pressure measurement result, a manipulation portion 112 manipulated for inputting various instructions for measurement, and a power supply portion 115 for supplying electric power to CPU 113 by an instruction of power ON from manipulation portion 112. CPU 113 serves as a blood pressure value calculating portion for calculating a blood pressure value.

Air system 121 for blood pressure measurement has a pressure sensor 122 having an output value changed in accordance with the pressure within air bag 150 (hereinafter, referred to as "cuff pressure"), a pump 123 for supplying the air to air bag 150, and a valve 124 that is opened or closed to evacuate the air from or seal the air in air bag 150. Pressure sensor 122 serves as a pressure detecting portion for detecting the cuff pressure. Oscillation circuit 125 outputs to CPU 113 a signal of oscillation frequency corresponding to the output value of pressure sensor 122. Pump driving circuit 126 controls driving of pump 123 based on a control signal supplied from CPU 113. Valve driving circuit 127 controls opening/closing of valve 124 based on a control signal supplied from CPU 113.

Figure 4:
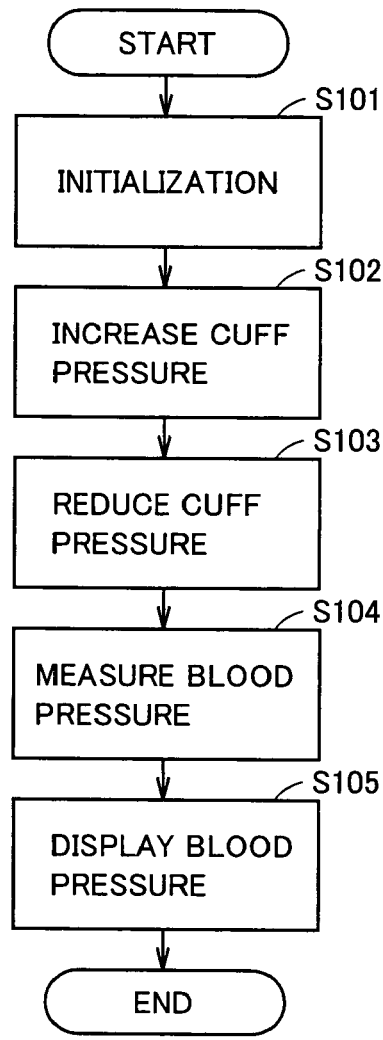
FIG. 4 is a flowchart illustrating the process flow of blood pressure measurement of the blood pressure monitor according to the first embodiment of the present invention.

FIG. 4 is a flowchart illustrating the process flow of blood pressure measurement by the blood pressure monitor according to the present embodiment. The program according to this flowchart is prestored in memory portion 114, and the blood pressure measuring process is carried out as CPU 113 reads out this program from memory portion 114 and executes the same.

As shown in FIG. 4, when a subject manipulates a manipulation button on manipulation portion 112 to turn the power ON, blood pressure monitor 100 is initialized (step S101). When it becomes a measurable state, CPU 113 starts driving of pump 123 to gradually increase the cuff pressure of air bag 150 (step S102). During the process of gradually increasing the pressure, when the cuff pressure reaches a prescribed level for measuring the blood pressure, CPU 113 stops pump 123, and gradually opens the closed valve 124 to evacuate the air from air bag 150, so as to gradually reduce the cuff pressure (step S103). In the present embodiment, the blood pressure is measured during the process of gradually decreasing the cuff pressure.

Next, CPU 113 calculates the blood pressure (systolic blood pressure, diastolic blood pressure) in a known manner (step S104). Specifically, during the process where the cuff pressure is gradually decreased, CPU 113 extracts pulse wave information based on the oscillation frequency obtained from oscillation circuit 125. It then calculates the blood pressure value from the pulse wave information extracted. The blood pressure value obtained in step S104 is displayed on display portion 111 (step S105). Although the measurement method described above is based on a so-called "decreasing-pressure measurement method" where the pulse waves are detected while the air bag is being decreased in pressure, it is of course possible to employ a so-called "increasing-pressure measurement method" where the pulse waves are detected while the air bag is being increased in pressure.

Blood pressure monitor 110 and cuff 130 for a blood pressure monitor of the present embodiment are characterized by the structure for securing air bag 150 arranged inside cuff 130 for a blood pressure monitor. Hereinafter, the securing structure of air bag 150 will be described in detail for respective examples with reference to the drawings.

EXAMPLE 1

Figure 5:
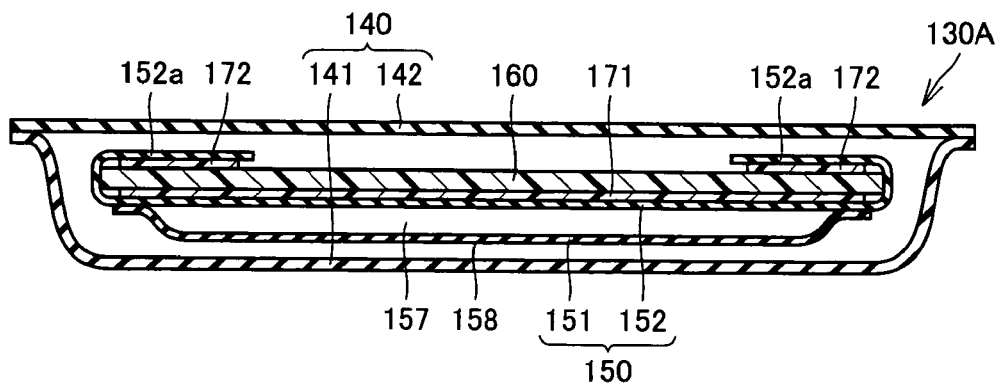
FIG. 5 is a schematic cross sectional view of a cuff for a blood pressure monitor of Example 1 based on the first embodiment of the present invention, taken along the line V-V shown in FIG. 2.
Figure 6:
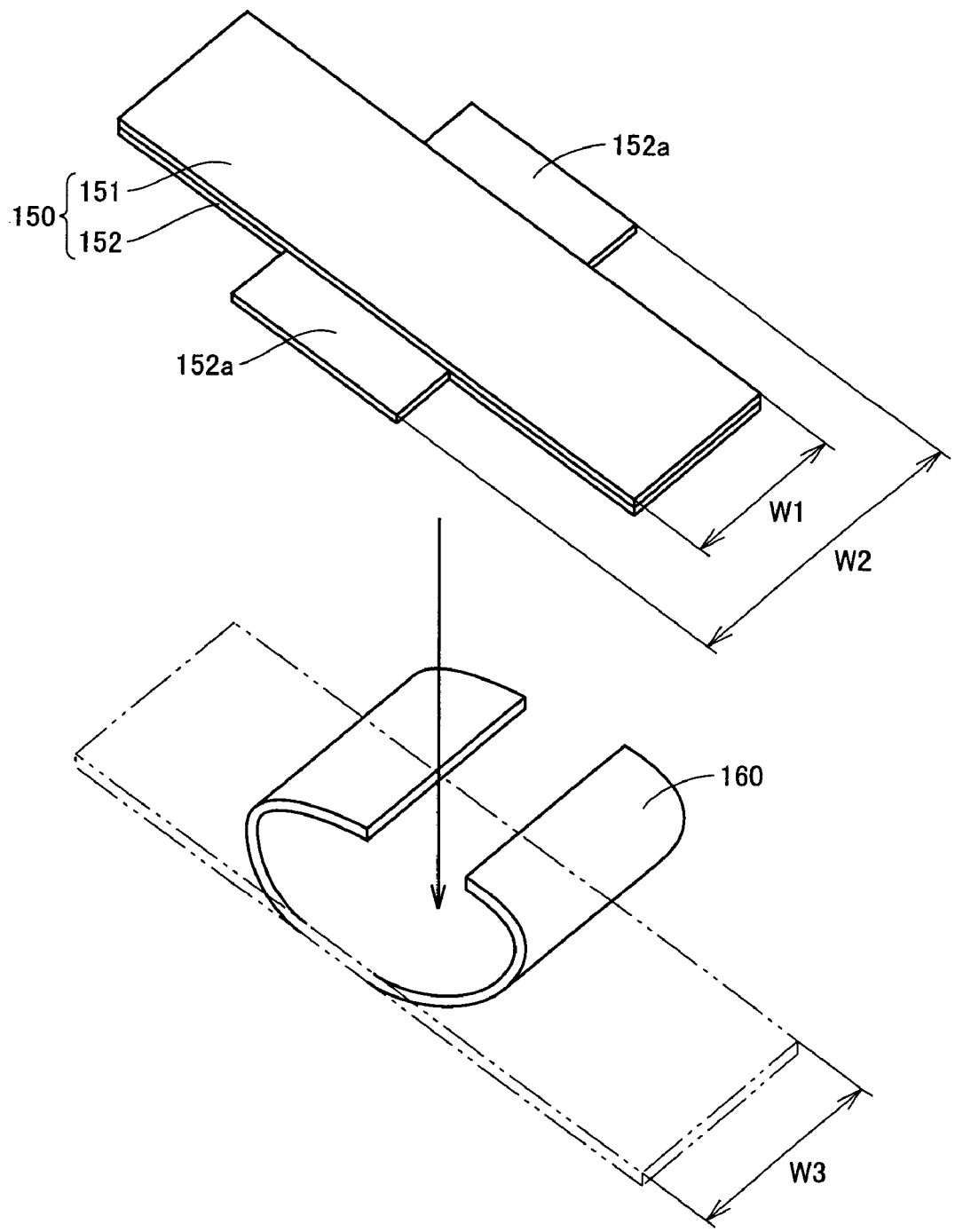
FIG. 6 is a schematic exploded diagram showing an assembled structure of an air bag and a curled elastic member contained in the cuff for a blood pressure monitor shown in FIG. 5.

FIG. 5 is a schematic cross sectional view of a cuff for a blood pressure monitor according to Example 1 based on the present embodiment, taken along the line V-V shown in FIG. 2. FIG. 6 is a schematic exploded diagram showing an assembled structure of an air bag and a curled elastic member contained in the cuff for a blood pressure monitor of the present example.

As shown in FIG. 5, the cuff 130A for a blood pressure monitor of the present example includes an air bag 150 identified as a fluid bag and a curled elastic member 160 identified as an elastic member provided inside a cover member 140 formed of an inner cover 141 and an outer cover 142. Air bag 150 is formed into a bag shape by laying a resin sheet 151 constituting an inner wall portion and a resin sheet 152 constituting an outer wall portion one on the other and melting and bonding their rims, and has an inflated/deflated space 157 therein. A surface on the wrist side of the inner wall portion of air bag 150 serves as a working face 158 for pressing the wrist. Curled elastic member 160 is located on an outer side of air bag 150, and has its inner peripheral surface attached via a double-faced tape 171 to an outer surface of the outer wall portion of air bag 150.

Air bag 150 has an engagement portion 152a that extends outwards from each side end portion in the width direction (direction parallel to the axial direction of the wrist in the fitted state of cuff 130A). To form engagement portion 152a, as shown in FIG. 6, a part of one resin sheet 152 out of two resin sheets 151, 152 laid one on the other is made to have a width W2 that is greater than a width WI of the other resin sheet 151 and greater than a width W3 of curled elastic member 160. That is, as shown in FIG. 6, engagement portion 152a is formed by a portion that protrudes from resin sheet 151 and curled elastic member 160 after two resin sheets 151, 152 are melted and bonded together into a bag shape and attached to the inner peripheral surface of curled elastic member 160.

As shown in FIG. 5, engagement portion 152a is folded back along the end face of curled elastic member 160 so as to cover a part of the outer peripheral surface of curled elastic member 160, and is secured to the outer peripheral surface of curled elastic member 160 using a double-faced tape 172. More specifically, engagement portion 152a is folded at each side end portion of air bag 150 toward the side of curled elastic member 160, and secured in an immovable manner as it is attached to curled elastic member 160 on the outer peripheral surface of curled elastic member 160, which is identified as a position on the side of curled elastic member 160 with respect to the outer surface of the outer wall portion of air bag 150.

Here, at the time of attaching air bag 150 to curled elastic member 160, curled elastic member 160 of a curved shape is spread flatly, as shown in FIG. 6. With curled elastic member 160 flatly spread, air bag 150 is attached to the inner side of curled elastic member 160, and engagement portion 152a is folded back. Spreading curled elastic member 160 flatly when folding back engagement portion 152a in this manner can improve workability of the assembly operation.

Figure 7:
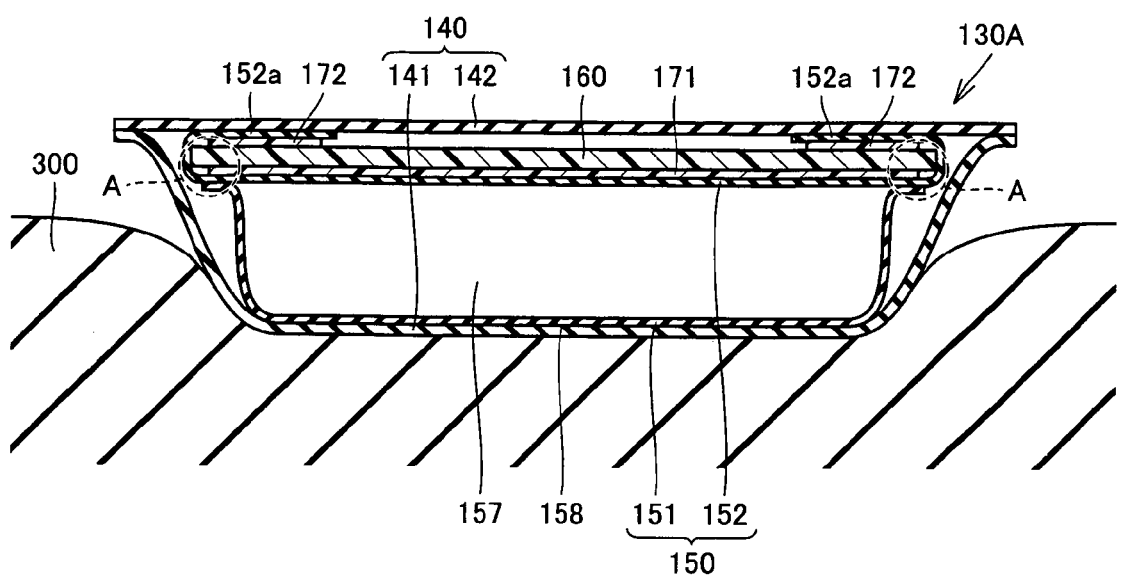
FIG. 7 is a schematic cross sectional view showing the state where the cuff for a blood pressure monitor shown in FIG. 5 is fitted on the wrist and the air bag is inflated.

FIG. 7 is a schematic cross sectional view showing the state where the cuff for a blood pressure monitor according to the present example having the above-described configuration is fitted on the wrist and the air bag is inflated. As shown in FIG. 7, in the inflated state of air bag 150, air bag 150 increases in size primarily with expansion of resin sheet 151 constituting the inner wall portion of air bag 150, since the outer surface of resin sheet 152 constituting the outer wall portion is attached to curled elastic member 160. At this time, rigidity of curled elastic member 160 as well as tensile strength of outer cover 142 regulates the behavior of air bag 150 intended to expand outwards, whereby inflated air bag 150 presses wrist 300 inwards.

Figure 26:
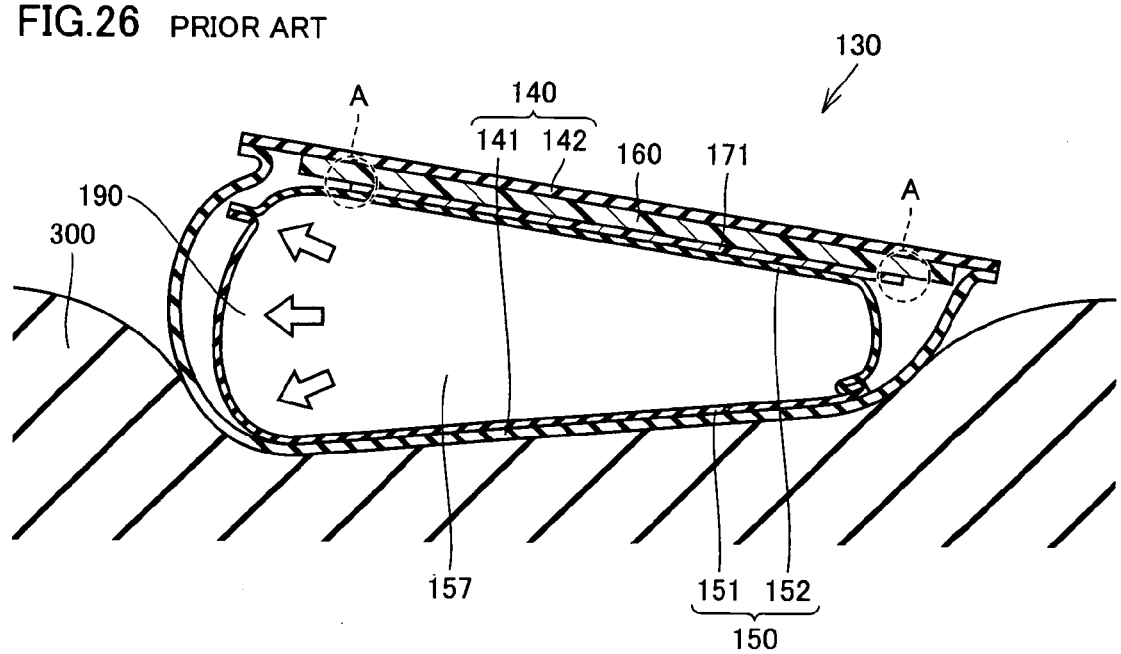
FIG. 26 is a schematic cross sectional view of the cuff for a blood pressure monitor and the wrist shown in FIG. 25, taken along the line XXVI-XXVI in FIG. 25.

Air bag 150 increases in thickness by a prescribed amount when inflated. With such increase in thickness, the risk of occurrence of the lateral displacement described above increases. However, in cuff 130A for a blood pressure monitor of the present example, engagement portion 152a is provided at each side end portion of air bag 150 as described above, and engagement portion 152a is secured to the outer peripheral surface of curled elastic member 160. Thus, even if a certain external force is applied to outer cover 142 of cover member 140 in the direction parallel to the axial direction of wrist 300, most of the force is applied to engagement portion 152a itself and to the attached portion of engagement portion 152a with curled elastic member 160. This considerably alleviates the force applied to the respective ends of the attached portion of the outer surface of the outer wall portion of air bag 150 and the inner peripheral surface of curled elastic member 160, shown by regions A in FIG. 7, and accordingly, the lateral displacement is unlikely to occur. Further, the force acting to cause peeling of air bag 150 from curled elastic member 160 in the relevant portions, which is noticeable in the above-described conventional cuff 130 for a blood pressure monitor (see FIG. 26), is alleviated as well, so that degradation in reliability of the attached portion can be prevented. Accordingly, it is possible to provide a highly reliable cuff for a blood pressure monitor that is unlikely to cause lateral displacement, and high avascularization performance is obtained even if the cuff width is narrowed.

It is noted that engagement portion 152a provided in air bag 150 is not particularly restricted in size, number, shape, or the resin sheet constituting engagement portion 152a. Although the case of increasing the width of resin sheet 152 out of the resin sheets constituting the air bag has been explained in the present example, the similar effect can be obtained even when the width of resin sheet 151 is increased. In cuff 130A for a blood pressure monitor of the present example, however, it is preferable that engagement portion 152a is provided approximately at a central portion in the longitudinal direction of air-bag 150. This configuration suppresses occurrence of displacement in the width direction of air bag 150 and curled elastic member 160 approximately at the central portion in the longitudinal direction of air bag 150, where the increase in size of air bag 150 in the thickness direction is greatest, and accordingly, occurrence of lateral displacement is prevented effectively.

EXAMPLE 2

Figure 8:
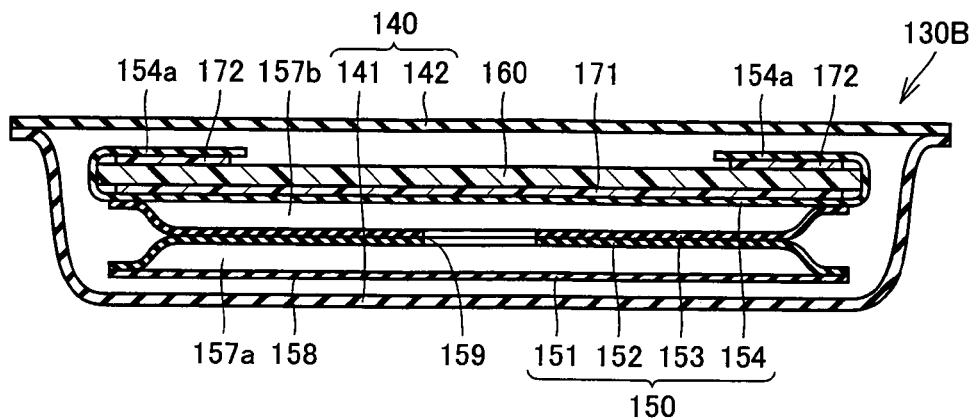
FIG. 8 is a schematic cross sectional view of a cuff for a blood pressure monitor according to Example 2 based on the first embodiment of the present invention.

FIG. 8 is a schematic cross sectional view of a cuff for a blood pressure monitor according to Example 2 based on the present embodiment. The portions similar to those of cuff 130A for a blood pressure monitor of Example 1 described above have the same reference characters allotted, and description thereof will not be repeated.

As shown in FIG. 8, the air bag 150 of the cuff 130B for a blood pressure monitor according to the present example is formed into a bag shape using four resin sheets 151, 152, 153 and 154. More specifically, two resin sheets 151, 152 of an approximately rectangular shape in two dimensions are laid one on the other and their rims are melted and bonded to form a first bag member having a first inflated/deflated space 157a therein. Further, two resin sheets 153, 154 of an approximately rectangular shape in two dimensions are laid one on the other and their rims are melted and bonded to form a second bag member having a second inflated/deflated space 157b therein. The first and second bag members are then laid one on the other, and melted and bonded at prescribed sites, to thereby form an integrated bag member of two layers having first inflated/deflated space 157a and second inflated/deflated space 157b. Of the four resin sheets, two resin sheets 152, 153 located in the region where the first and second bag members are connected to each other have holes bored in advance at prescribed positions corresponding to each other. These holes form a communication hole 159 through which first inflated/deflated space 157a communicates with second inflated/deflated space 157b after formation of air bag 150.

Resin sheet 151 forms an inner wall portion located on an inner side in the state where cuff 130B for a blood pressure monitor is fitted on the wrist. Resin sheet 154 forms an outer wall portion located on the outer side than the inner wall portion in the state where cuff 130B is fitted on the wrist. Of the inner wall portion of air bag 150, the surface on the wrist side functions as a working face 158 for pressing the wrist. Resin sheets 152 and 153 are melted and bonded together to join the first and second bag members, as described above. Resin sheets 152 and 153 constitute side wall portions of air bag 150 at the respective end portions in the width direction located on an outer side than the relevant bonded portion, and constitute a connecting portion located inside air bag 150 at the position inner than the bonded portion. The side wall portions each function as a gusset that expands in the thickness direction when air bag 150 is inflated. The connecting portion is for guiding the side wall portions serving as the gussets such that they are surely folded inwards when air bag 150 changes from the inflated state to the deflated state.

Air bag 150 has an engagement portion 154a that extends from each side end portion in the width direction toward the outside. To form this engagement portion 154a, of four resin sheets 151, 152, 153 and 154 laid one on another, a part of resin sheet 154 located outermost is made to have a width that is greater than the widths of other resin sheets 151, 152, 153 and the width of curled elastic member 160. Engagement portion 154a is folded along the end face of curled elastic member 160 so as to cover a part of the outer peripheral surface of curled elastic member 160, and is secured to the outer peripheral surface of curled elastic member 160 using a double-faced tape 172.

With this configuration as well, a highly reliable cuff for a blood pressure monitor suppressing lateral displacement can be provided, as in Example 1 described above, and high avascularization performance is obtained even if the cuff is narrowed in width.

It is noted that engagement portion 154a provided in air bag 150 is not particularly restricted in size, number, shape, or the resin sheet constituting engagement portion 154a. However, in cuff 130B for a blood pressure monitor of the present example as well, it is preferable that engagement portion 154a is provided approximately at a central portion in the longitudinal direction of air bag 150, for the same reasons as in cuff 130A for a blood pressure monitor of Example 1 described above.

Figure 9:
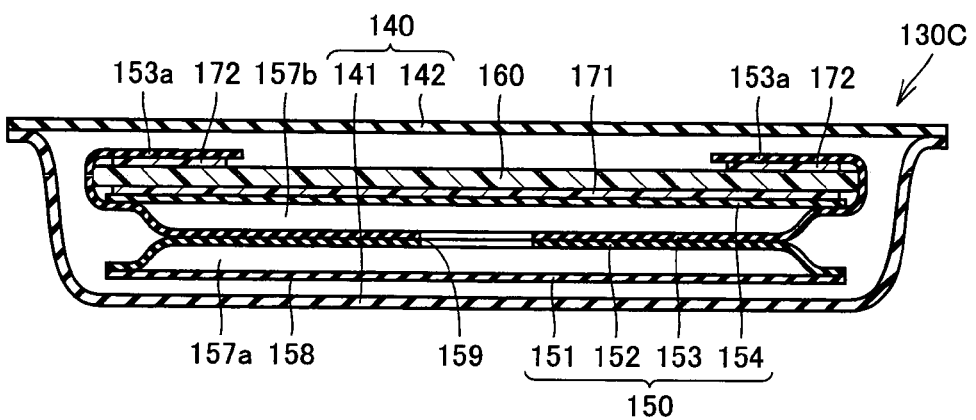
FIG. 9 is a schematic cross sectional view showing a modification of the cuff for a blood pressure monitor of Example 2 based on the first embodiment of the present invention.

FIG. 9 is a schematic cross sectional view showing a modification of the cuff for a blood pressure monitor of the present example. As shown in FIG. 9, in the cuff 130C for a blood pressure monitor according to the present modification, a part of resin sheet 153 located second from the outside among four resin sheets 151, 152, 153 and 154 laid one on another, is increased in width than other resin sheets 151, 152, 154 and curled elastic member 160, to form an engagement portion 153a. Engagement portion 153a is folded along the end face of curled elastic member 160 to cover a part of the outer peripheral surface of curled elastic member 160, and is secured to the outer peripheral surface of curled elastic member 160 using a double-faced tape 172, to thereby prevent occurrence of lateral displacement.

Figure 10:
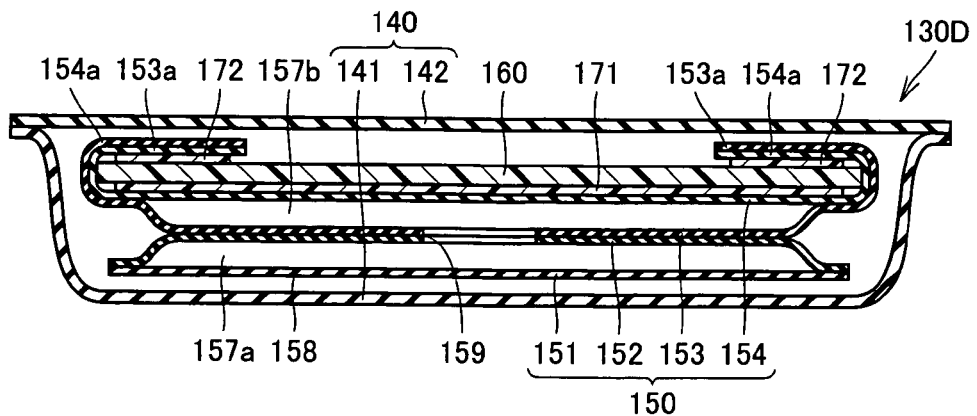
FIG. 10 is a schematic cross sectional view showing another modification of the cuff for a blood pressure monitor of Example 2 based on the first embodiment of the present invention.

FIG. 10 is a schematic cross sectional view showing another modification of the cuff for a blood pressure monitor according to the present example. As shown in FIG. 10, in the cuff 130D for a blood pressure monitor of the present modification, a part of resin sheet 154 located outermost and a part of resin sheet 153 located second from the outside among four resin sheets 151, 152, 153 and 154 laid one on another, are made greater in width than other resin sheets 151, 152 and curled elastic member 160, to form engagement portions 153a and 154a. Engagement portions 153a, 154a are folded along the end face of curled elastic member 160 to cover a part of the outer peripheral surface of curled elastic member 160, and secured to the outer peripheral surface of curled elastic member 160 using a double-faced tape 172, to prevent occurrence of lateral displacement.

As described above, in the case of laying a plurality of resin sheets one on another to provide a multi-layered air bag structure having a multiple layers of inflated/deflated spaces as shown in FIGS. 8-10, the engagement portion may be formed using any of the resin sheets, or may be formed using more than one of the resin sheets, for which a large number of variations are conceivable.

EXAMPLE 3

Figure 11:
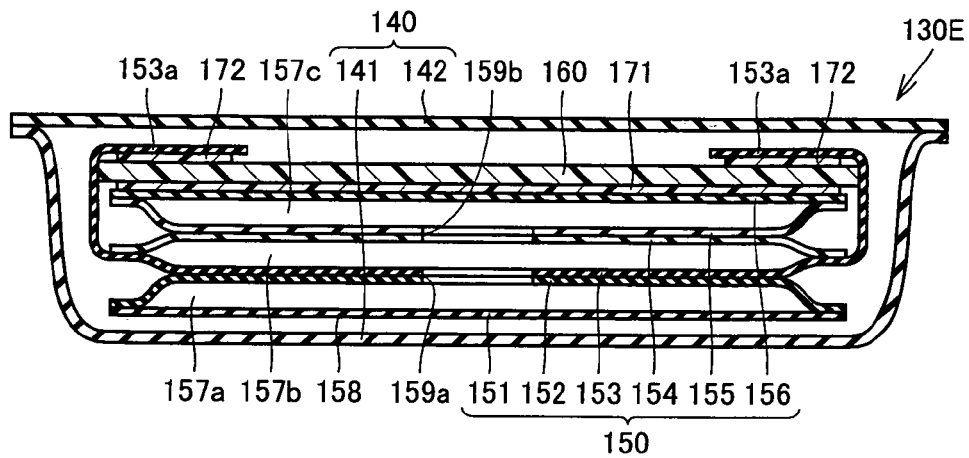
FIGS. 11-14 are schematic cross sectional views of cuffs for a blood pressure monitor according to Examples 3-6, respectively, based on the first embodiment of the present invention.

FIG. 11 is a schematic cross sectional view of a cuff for a blood pressure monitor according to Example 3 based on the present embodiment. The portions similar to those of cuff 130A for a blood pressure monitor of Example 1 described above have the same reference characters allotted, and description thereof will not be repeated.

As shown in FIG. 11, the air bag 150 of the cuff 130E for a blood pressure monitor according to the present example is formed into a bag shape using six resin sheets 151, 152, 153, 154, 155 and 156. More specifically, two resin sheets 151, 152 of an approximately rectangular shape in two dimensions are laid one on the other and their rims are melted and bonded to form a first bag member having a first inflated/deflated space 157a therein. Two resin sheets 153, 154 of an approximately rectangular shape in two dimensions are laid one on the other and their rims are melted and bonded to form a second bag member having a second inflated/deflated space 157b therein. Further, two resin sheets 155, 156 of an approximately rectangular shape in two dimensions are laid one on the other and their rims are melted and bonded to form a third bag member having a third inflated/deflated space 157c therein. The first, second and third bag members are then laid one on another, and melted and bonded at prescribed sites, to thereby form an integrated bag member of three layers having first inflated/deflated space 157a, second inflated/deflated space 157b and third inflated/deflated space 157c. Of the six resin sheets, two resin sheets 152, 153 located in the region where the first and second bag members are connected to each other have holes bored in advance at prescribed positions corresponding to each other. These holes form a communication hole 159a through which first inflated/deflated space 157a communicates with second inflated/deflated space 157b after formation of air bag 150. Further, of the six resin sheets, two resin sheets 154, 155 located in the region where the second and third bag members are connected have holes bored in advance at prescribed positions corresponding to each other, which form a communication hole 159b through which second inflated/deflated space 157b communicates with third inflated/deflated space 157c after formation of air bag 150.

Resin sheet 151 forms an inner wall portion located on an inner side when cuff 130E for a blood pressure monitor is fitted on the wrist. Resin sheet 156 forms an outer wall portion located on the outer side than the inner wall portion in the state where cuff 130E is fitted on the wrist. Of the inner wall portion of air bag 150, the surface on the wrist side functions as a working face 158 for pressing the wrist. Resin sheets 152 and 153 are melted and bonded together so as to join the first and second bag members, as described above. Resin sheets 152 and 153 constitute side wall portions of air bag 150 at the respective end portions in the width direction located on an outer side than the relevant bonded portion, and constitute a connecting portion located inside air bag 150 at the position inner than the bonded portion. Further, resin sheets 154 and 155 are melted and bonded together so as to join the second and third bag members, as described above. Resin sheets 154 and 155 constitute side wall portions of air bag 150 at the respective end portions in the width direction located on an outer side than the relevant bonded portion, and constitute a connecting portion located inside air bag 150 at the position inner than the bonded portion. The side wall portions each function as a gusset that expands in the thickness direction when air bag 150 is inflated. The connecting portions are for guiding the side wall portions serving as the gussets such that they are surely folded inwards when air bag 150 changes from the inflated state to the deflated state.

Air bag 150 has an engagement portion 153a that extends from each side end portion in the width direction toward the outside. To form this engagement portion 153a, of six resin sheets 151, 152, 153, 154, 155 and 156 laid one on another, a part of resin sheet 153 forming inflated/deflated space 157b is made to have a width that is greater than the widths of other resin sheets 151, 152, 154, 155, 156 and the width of curled elastic member 160. Engagement portion 153a is folded along the end face of curled elastic member 160 so as to cover a part of the outer peripheral surface of curled elastic member 160, and is secured to the outer peripheral surface of curled elastic member 160 using a double-faced tape 172.

With this configuration as well, a highly reliable cuff for a blood pressure monitor suppressing lateral displacement can be provided, and high avascularization performance is obtained even if the cuff is narrowed in width, as in Example 1 described above. Particularly, since the engagement portion is provided to extend from each side end of the second bag member arranged in the middle of the three bag members laid one on another, prevention of lateral displacement of the air bag and maintenance of sufficient avascularization performance can both be realized effectively. If the engagement portion is provided at a part of the third bag member located outermost, restraint of the first and second bag members at each side end portion in the width direction by the engagement portion will be insufficient, in which case lateral displacement is likely to occur. If the engagement portion is provided at a part of the first bag member located innermost, inflation in the thickness direction of air bag 150 at each side end portion in the width direction will be insufficient, in which case the wrist may not be pressed satisfactorily.

It is noted that engagement portion 153a provided in air bag 150 is not particularly restricted in size, number, shape, or the resin sheet constituting engagement portion 153a. However, in cuff 130E for a blood pressure monitor of the present example as well, it is preferable that engagement portion 153a is provided approximately at a central portion in the longitudinal direction of air bag 150, for the same reasons as in cuff 130A for a blood pressure monitor of Example 1 described above, as well as for the following reason.

Generally, a wrist blood pressure monitor is configured such that an approximately central portion in the longitudinal direction of the air bag is positioned on the palm side of the wrist in the state where the cuff is wound around the wrist. Under the skin of the palm side portion of the wrist, a tendon relatively harder than those in the other potions of the wrist is located. Thus, when engagement portion 153a is provided approximately at the central portion in the longitudinal direction of air bag 150 as described above, an influence of the engagement portion on pressing and avascularization of the artery can be reduced compared to the case of providing engagement portion 153a at another site. As such, it is possible to minimize the adverse effect of degradation in performance of pressing and avascularization attributable to provision of engagement portion 153a.

EXAMPLE 4

Figure 12:
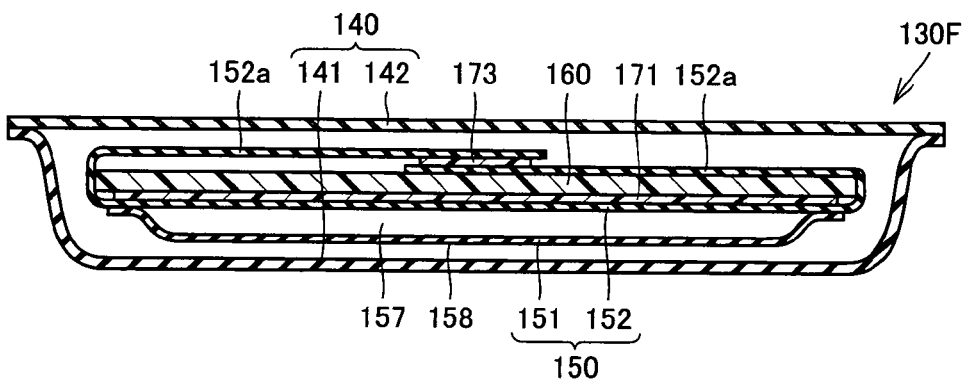

FIG. 12 is a schematic cross sectional view of a cuff for a blood pressure monitor according to Example 4 based on the present embodiment. The portions similar to those of cuff 130A for a blood pressure monitor of Example 1 described above have the same reference characters allotted, and description thereof will not be repeated.

As shown in FIG. 12, in the cuff 130F for a blood pressure monitor according to the present example, engagement portion 152a of cuff 130A for a blood pressure monitor of Example 1 is further extended in the width direction such that, when engagement portion 152a is folded along the end face of curled elastic member 160 and positioned on the outer peripheral surface of curled elastic member 160, the pair of engagement portions 152a extended from the respective side end portions of air bag 150 come to overlap with each other on the outer peripheral surface of curled elastic member 160. Unlike the case of cuff 130A for a blood pressure monitor of Example 1 where engagement portion 152a is secured to curled elastic member 160, in the present example, the pair of engagement portions 152a are secured to each other via a double-faced tape 173. In this manner, in the cross section in the width direction of cuff 130F for a blood pressure monitor, resin sheet 152 surrounds curled elastic member 160. That is, the pair of engagement portions 152a are folded at the respective side end portions of air bag 150 toward curled elastic member 160, and they are secured in an immovable manner as they are attached to each other on the outer peripheral surface of curled elastic member 160, which is located on the side of curled elastic member 160 with respect to the outer surface of the outer wall portion of air bag 150.

With this configuration as well, it is possible to provide a highly reliable cuff for a blood pressure monitor that is unlikely to cause lateral displacement, and high avascularization performance is obtained even if the cuff is narrowed in width, as in the case of Example 1 described above.

It is noted that engagement portion 152a provided in air bag 150 is not particularly restricted in size, number, shape, or the resin sheet constituting engagement portion 152a. However, in cuff 130F for a blood pressure monitor of the present example as well, it is preferable that engagement portion 152a is provided approximately at a central portion in the longitudinal direction of air bag 150, for the same reasons as in cuff 130A for a blood pressure monitor of Example 1 described above.

EXAMPLE 5

Figure 13:
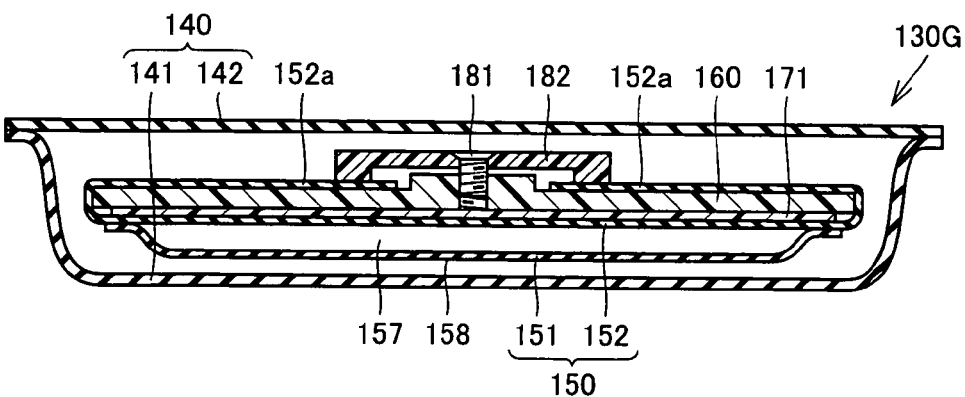

FIG. 13 is a schematic cross sectional view of a cuff for a blood pressure monitor according to Example 5 based on the present embodiment. The portions similar to those of cuff 130A for a blood pressure monitor of Example 1 described above have the same reference characters allotted, and description thereof will not be repeated.

As shown in FIG. 13, in the cuff 130G for a blood pressure monitor according to the present example, engagement portion 152a provided at each side end portion of air bag 150 is not secured to the outer peripheral surface of curled elastic member 160 using a double-faced tape, but pressed and secured via a plate 182. More specifically, as shown in FIG. 13, engagement portion 152a is folded back along the end face of curled elastic member 160 and positioned on the outer peripheral surface of curled elastic member 160. Plate 182, which is attached to the outer peripheral surface of curled elastic member 160 by a screw 181, is used to sandwich engagement portion 152a between plate 182 and the outer peripheral surface of curled elastic member 160 and press and secure engagement portion 152a therebetween. In this manner, the pair of engagement portions 152a are folded at the respective side end portions of air bag 150 toward curled elastic member 160, and secured to curled elastic member 160 in an immovable manner on the outer peripheral surface of curled elastic member 160, which is located on the side of curled elastic member 160 with respect to the outer surface of the outer wall portion of air bag 150.

With this configuration as well, it is possible to provide a highly reliable cuff for a blood pressure monitor that is unlikely to cause lateral displacement, and high avascularization performance is obtained even if the cuff is narrowed in width, as in Example 1 described above.

It is noted that engagement portion 152a provided in air bag 150 is not particularly restricted in size, number, shape, or the resin sheet constituting engagement portion 152a. However, in cuff 130G for a blood pressure monitor of the present example as well, it is preferable that engagement portion 152a is provided approximately at a central portion in the longitudinal direction of air bag 150, for the same reasons as in cuff 130A for a blood pressure monitor of Example 1 described above.

EXAMPLE 6

Figure 14:
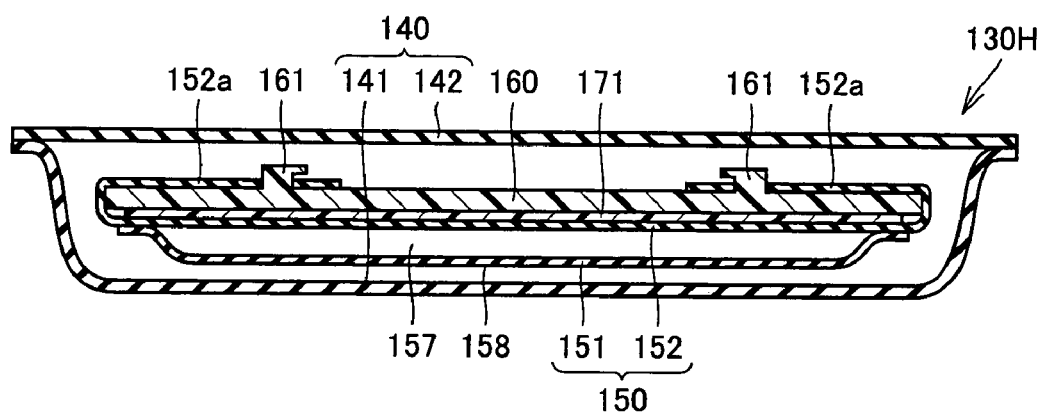

FIG. 14 is a schematic cross sectional view of a cuff for a blood pressure monitor according to Example 6 based on the present embodiment. The portions similar to those of cuff 130A for a blood pressure monitor of Example 1 described above have the same reference characters allotted, and description thereof will not be repeated.

As shown in FIG. 14, in the cuff 130H for a blood pressure monitor according to the present example, engagement portion 152a provided at each side end portion of air bag 150 is not secured to the outer peripheral surface of curled elastic member 160 using a double-faced tape, but secured via a hook 161 erected on the outer peripheral surface of curled elastic member 160. More specifically, as shown in FIG. 14, engagement portions 152a are each provided with a hole at a prescribed position, and folded back along the end face of curled elastic member 160 and positioned on the outer peripheral surface of curled elastic member 160. The holes provided on respective engagement portions 152a are hooked onto the corresponding hooks 161 provided on the outer peripheral surface of curled elastic member 160, to secure engagement portions 152a to curled elastic member 160. That is, the pair of engagement portions 152a are folded at the respective side end portions of air bag 150 toward curled elastic member 160, and secured to curled elastic member 160 in an immovable manner on the outer peripheral surface of curled elastic member 160, which is located on the side of curled elastic member 160 with respect to the outer surface of the outer wall portion of air bag 150.

With this configuration as well, it is possible to provide a highly reliable cuff for a blood pressure monitor that is unlikely to cause lateral displacement, and high avascularization performance is obtained even if the cuff is narrowed in width, as in Example 1 described above.

It is noted that engagement portion 152a provided in air bag 150 is not particularly restricted in size, number, shape, or the resin sheet constituting engagement portion 152a. However, in cuff 130H for a blood pressure monitor of the present example as well, it is preferable that engagement portion 152a is provided approximately at a central portion in the longitudinal direction of air bag 150, for the same reasons as in cuff 130A for a blood pressure monitor of Example 1 described above.

Figure 15:
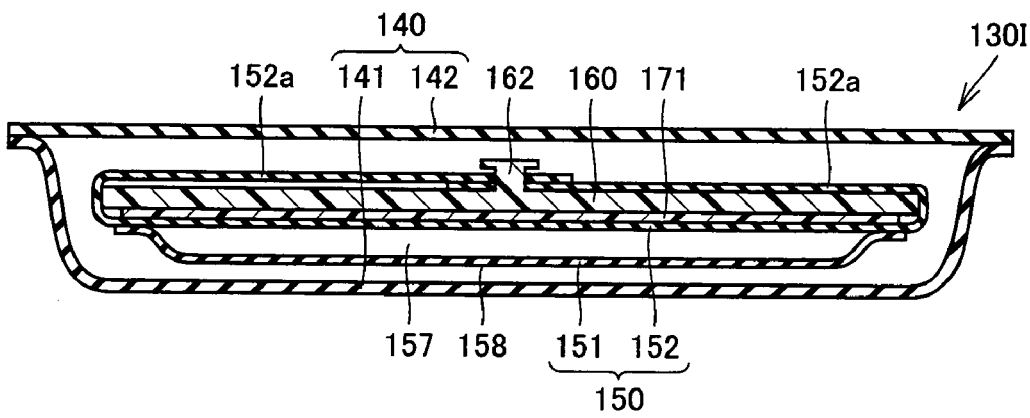
FIG. 15 is a schematic cross sectional view showing a modification of the cuff for a blood pressure monitor of Example 6 based on the first embodiment of the present invention.

FIG. 15 is a schematic cross sectional view showing a modification of the cuff for a blood pressure monitor according to the present example. As shown in FIG. 15, in the cuff 130I for a blood pressure monitor of the present modification, the pair of hooks 161 provided on the outer peripheral surface of curled elastic member 160 in cuff 130H for a blood pressure monitor of the present example described above are replaced with a common hook 162, and the holes provided on the respective engagement portions 152a are hooked onto hook 162 to secure engagement portions 152a to curled elastic member 160, to thereby prevent occurrence of lateral displacement.

In the first embodiment described above, explanation was made about the case where a plurality of resin sheets are laid one on another and melted and bonded to form an air bag. However, the air bag does not necessarily have to be formed using a plurality of resin sheets, but may be formed using a single sheet of a cylindrical shape. The present invention is applicable to such a case as well.

Further, in the first embodiment, explanation was made about the case where a double-faced tape is used to attach the curled elastic member to the air bag. However, they do not necessarily have to be secured by adhesion or the like, but they may be secured using another method, or they may be left completely unfixed to each other.

Furthermore, in the first embodiment, explanation was made about the case where the present invention is applied to a cuff for use in a wrist blood pressure monitor assuming a wrist as the measurement site. However, the present invention is applicable to a cuff for a blood pressure monitor of any type, including the upper arm type and the finger type.

Second Embodiment

Figure 16:
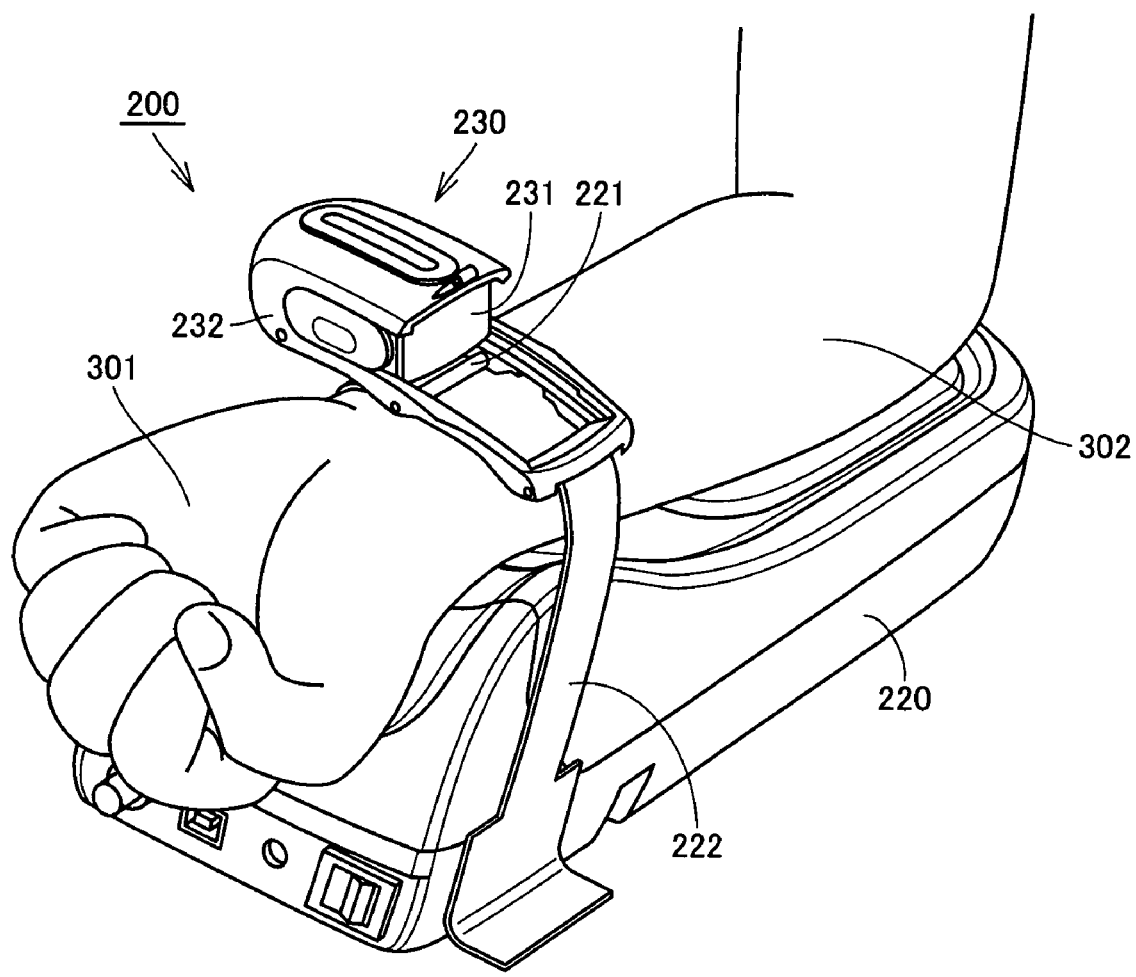
FIG. 16 is a perspective view of a pulse wave detector according to a second embodiment of the present invention, showing the state fitted on the living body.
Figure 17:
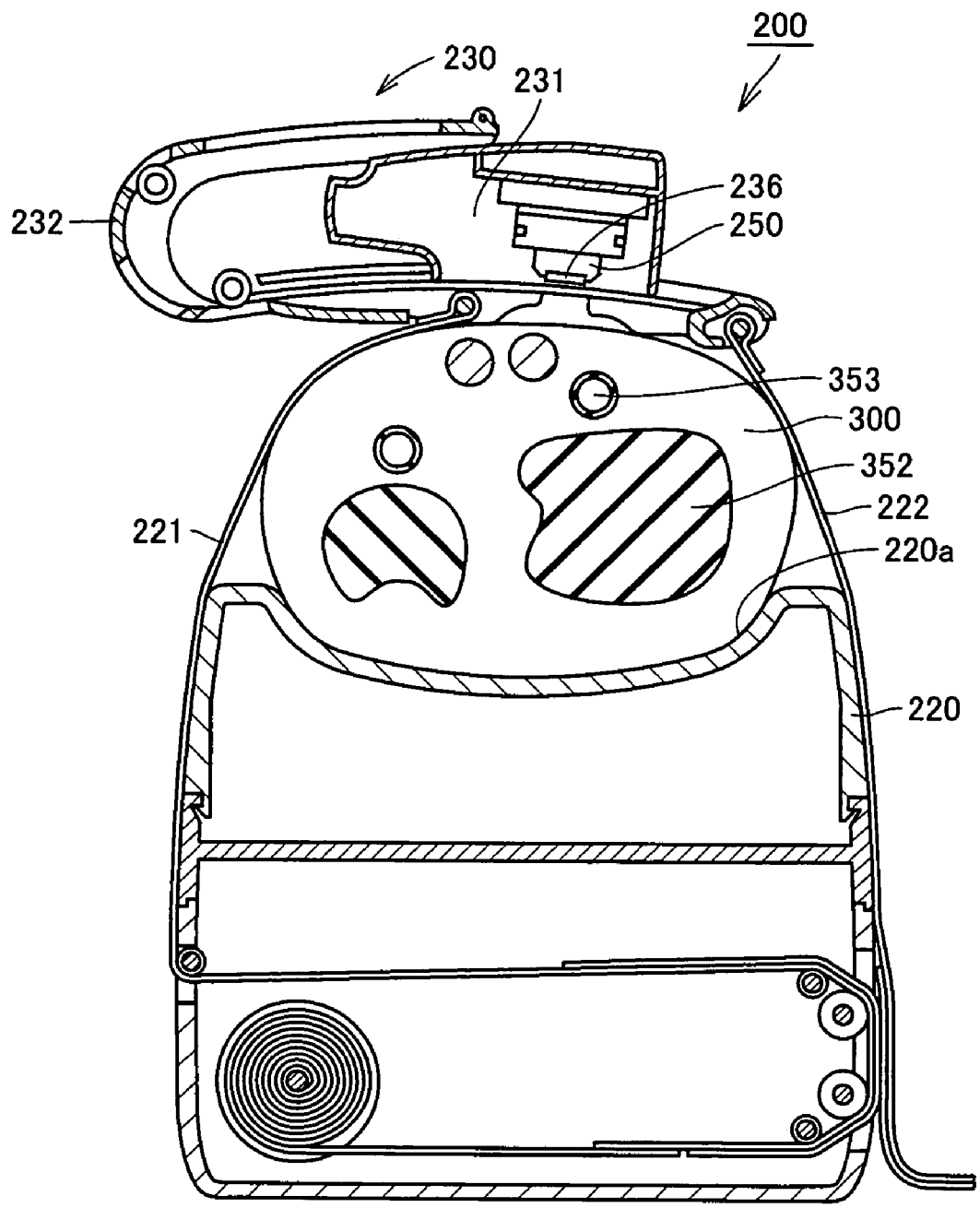
FIG. 17 is a schematic cross sectional view of the pulse wave detector in the state shown in FIG. 16.
Figure 18:
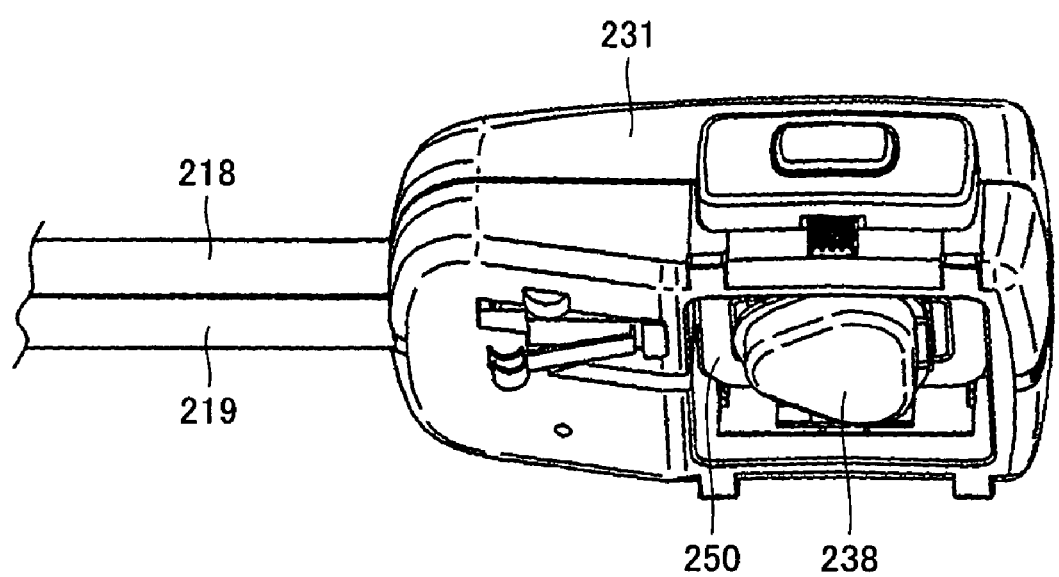
FIG. 18 is a perspective view of a sensor unit of the pulse wave detector according to the second embodiment of the present invention.

FIG. 16 is a perspective view of a pulse wave detector according to a second embodiment of the present invention, showing the state fitted on a living body. FIG. 17 is a schematic cross sectional view of the pulse wave detector in the state shown in FIG. 16. FIG. 18 is a perspective view of a sensor unit of the pulse wave detector of the present embodiment.

Figure 19:
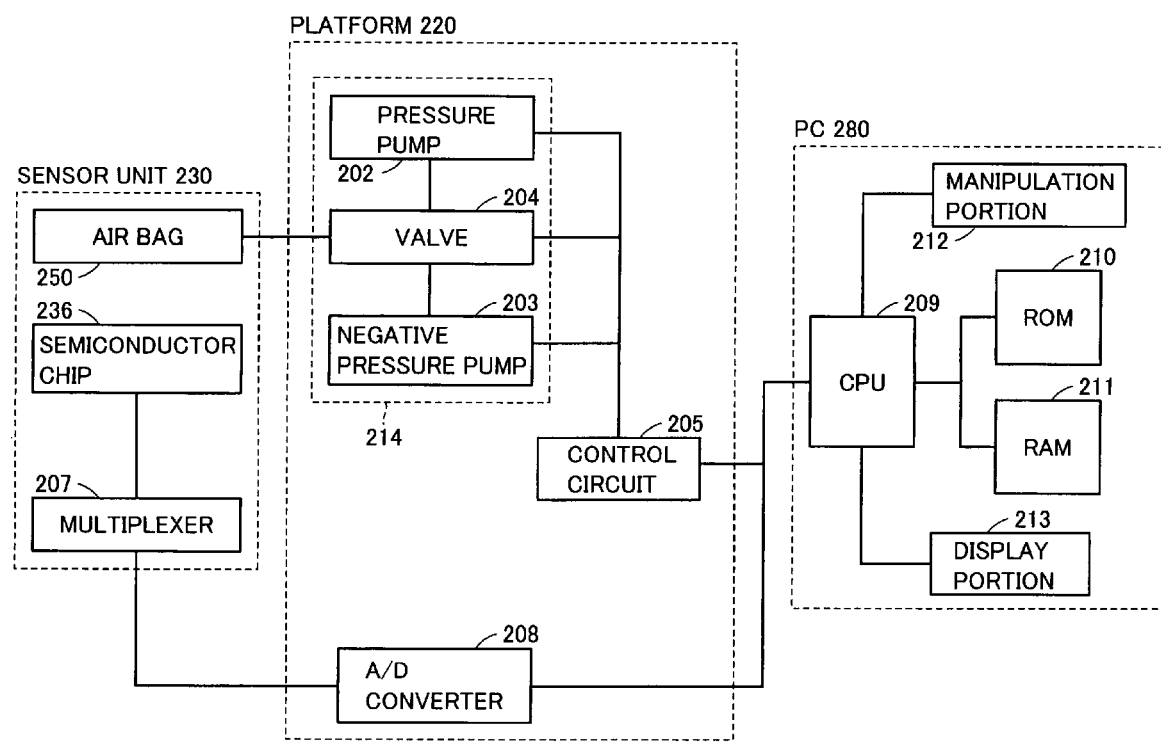
FIG. 19 is a block diagram showing a configuration of the pulse wave detector according to the second embodiment of the present invention.

As shown in FIGS. 16 and 17, the pulse wave detector 200 according to the present embodiment includes a sensor unit 230 having a semiconductor chip 236 on which semiconductor pressure sensors identified as a pressure-sensitive portion are arranged in an array, a platform 220 and fastening bands 221, 222 serving as a living body securing tool for securing the posture of the living body, and a PC (Personal Computer) 280 (see FIG. 19).

Sensor unit 230 is formed of a case member 231 having semiconductor chip 236, and a base member 232 supporting case member 231 in a slidable manner. An air bag 250, identified as a fluid bag serving as a pressing member, is arranged inside case member 231, and semiconductor chip 236 described above is attached to the lower surface of air bag 250. As shown in FIG. 18, an opening is provided at the lower surface of case member 231, through which semiconductor chip 236 is lowered as air bag 250 is inflated, and thus, the semiconductor pressure sensors are pressed against the surface of wrist 300 at the time of measurement. It is noted that semiconductor chip 236 is covered with a protective cap 238 for prevention of damage, as shown in FIG. 18.

As shown in FIGS. 16 and 17, platform 220 is a box-shaped member having a concave portion 220a on the upper surface where a part of the arm of the subject from the elbow to the wrist can be rested, which contains therein a pressure pump 202, a negative pressure pump 203 and a valve 204 that are identified as an inflating/deflating portion 214 (see FIG. 19). A control circuit 205 for controlling inflating/deflating portion 214 is also arranged inside platform 220.

An input/output terminal is provided on the front surface of platform 220, and control circuit 205 arranged inside platform 220 is connected to PC 280 in a communicable manner via a communication cable such as a USB (Universal Serial Bus) cable. Further, sensor unit 230 and platform 220 are connected via a signal cable 218 and an air tube 219 (see FIG. 18). Fastening bands 221, 222 having elasticity connect sensor unit 230 to platform 220.

In pulse wave detector 200 of the above-described configuration, as shown in FIGS. 16 and 17, the arm from the elbow to the wrist is rested on concave portion 220a of platform 220, and fastening bands 221, 222 are used to secure sensor unit 230 to the wrist portion of the arm, to thereby fit pulse wave detector 200 on the living body. Air bag 250 contained in sensor unit 230 is then inflated to press semiconductor chip 236 attached to the lower surface of air bag 250 against a position of the wrist corresponding to a radial artery 353, for detection of pulse waves.

FIG. 19 is a block diagram showing a configuration of the pulse wave detector according to the present embodiment. As shown in FIG. 19, sensor unit 230 includes semiconductor chip 236 having a plurality of semiconductor pressure sensors formed of diaphragms and a resistance bridge circuit for detecting pulse pressure, a multiplexer 207 serving as a signal extracting portion for performing time-division multiplexing of a plurality of voltage signals output from the semiconductor pressure sensors and selectively deriving the same, and air bag 250 that is pressurized and adjusted for pressing the semiconductor pressure sensors against the wrist.

Platform 220 includes pressure pump 202 for increasing the internal pressure of air bag 250, negative pressure pump 203 for reducing the pressure, valve 204 for selectively connecting either pressure pump 202 or negative pressure pump 203 to air tube 219, control circuit 205 controlling operations of pressure pump 202, negative pressure pump 203 and valve 204, and an A/D converter 208 identified as an A/D converting portion for converting an output signal derived from sensor unit 230 to digital data. Pressure pump 202, negative pressure pump 203 and valve 204 function as an inflating/deflating portion for inflating and deflating air bag 250 identified as a fluid bag.

PC 280 has a CPU 209 identified as a processing portion for executing various kinds of processing including calculations for controlling pulse wave detector 200 in a centralized manner, a ROM (Read Only Memory) 210 and a RAM (Random Access Memory) 211 for storing data and programs for controlling pulse wave detector 200, a manipulation portion 212 provided in a manipulable manner and manipulated for inputting various information, and a display portion 213 formed of an LCD (Liquid Crystal Display) or the like for externally outputting various information such as a measurement result of the pulse waves. It is noted that CPU 209 also functions as a pulse wave measuring portion for measuring pulse waves based on pressure information detected by the semiconductor pressure sensor identified as the pressure-sensitive portion.

Figure 20:
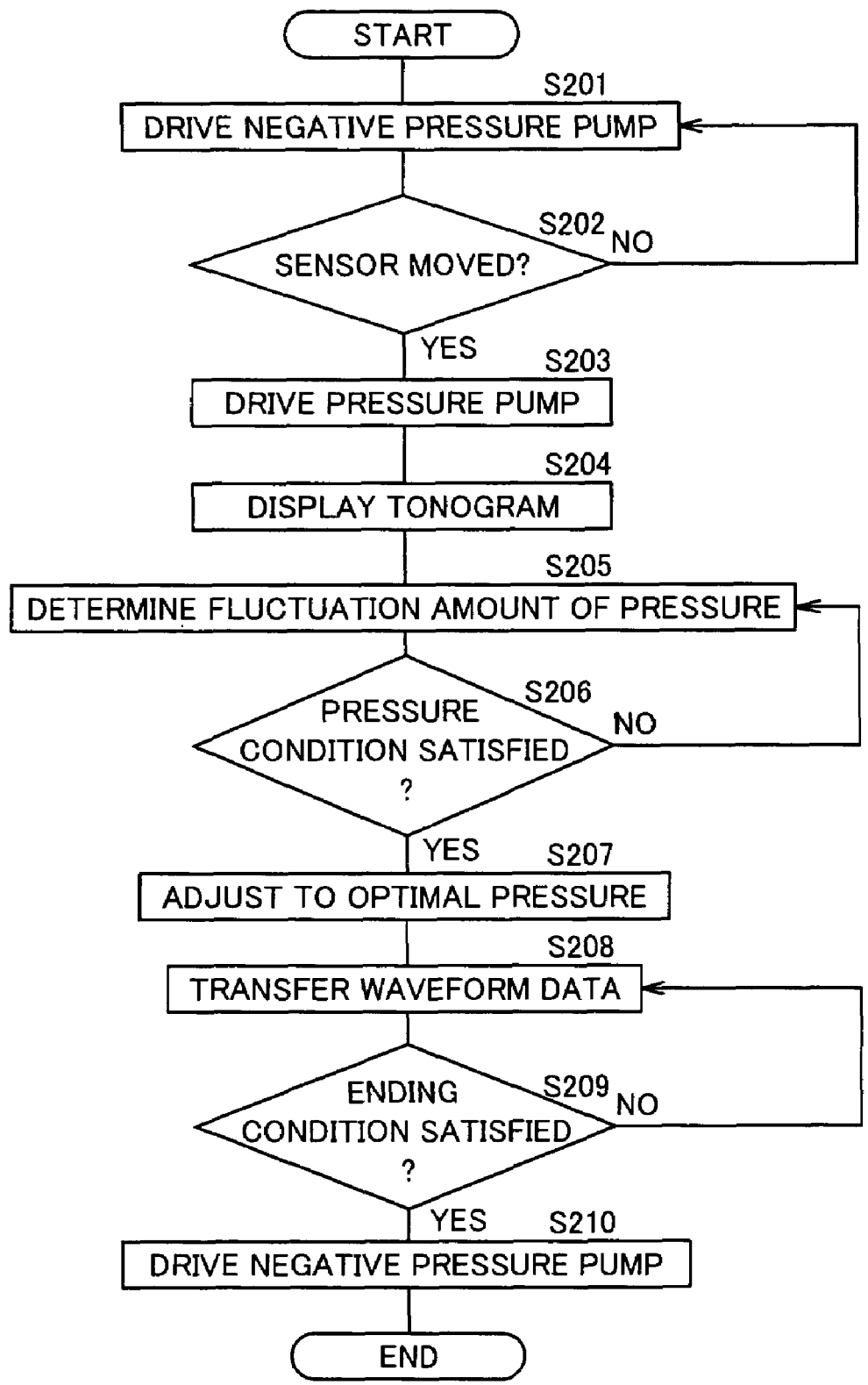
FIG. 20 is a flowchart illustrating a process procedure for measuring pulse waves in the pulse wave detector according to the second embodiment of the present invention.

FIG. 20 is a flowchart illustrating a process procedure for measuring pulse waves in the pulse wave detector according to the present embodiment. A program according to this flowchart and data to be referred to at the time of execution of the program are prestored in ROM 210 or RAM 211, and the pulse wave measuring process is carried out as CPU 209 reads and executes the program while referring to the data as appropriate.

Firstly, when a user turns on a power supply switch (not shown), CPU 209 instructs control circuit 205 to drive negative pressure pump 203. Control circuit 205 switches valve 204 to the side of negative pressure pump 203 based on the instruction, to drive negative pressure pump 203 (step S201).

Negative pressure pump 203, when driven, operates to make the internal pressure of air bag 250 sufficiently lower than the atmospheric pressure via valve 204, and thus, semiconductor chip 236 moves upwards within sensor unit 230. This prevents semiconductor chip 236 from accidentally protruding to cause malfunction or breakdown.

Thereafter, when the user fits sensor unit 230 on the wrist as shown, e.g., in FIG. 16 and turns on a start button (not shown), it is determined whether semiconductor chip 236 has moved or not, i.e., whether case member 231 of sensor unit 230 has been slided along a slide groove so that it is positioned on the surface of the wrist (step S202). A microswitch (not shown) is provided inside the casing of sensor unit 230 for detecting the sliding movement, and CPU 209 determines whether semiconductor chip 236 has moved or not based on a detection signal of the microswitch.

If it is not determined that it has moved (NO in step S202), the process of step S201 is repeated. If it is determined that it has moved (YES in step S202), CPU 209 instructs control circuit 205 to drive pressure pump 202. In response to this instruction, control circuit 205 switches valve 204 to the side of pressure pump 202, to drive pressure pump 202 (step S203). As such, the internal pressure of air bag 250 increases, and semiconductor chip 236 moves downwards toward the wrist and is pressed against the surface of the wrist.

When semiconductor chip 236 is pressed against the surface of the wrist, pressure information of the voltage signal from the semiconductor pressure sensor is derived via multiplexer 207, which is then converted into digital information by A/D converter 208 and supplied to CPU 209. CPU 209 uses the digital information to produce a tonogram, and displays it on display portion 213 (step S204).

Next, in order to detect pulse waves based on pressure information input from the semiconductor pressure sensor, CPU 209 calculates the amount of change in pressing level by air bag 250, and compares the calculated amount of change with a predetermined amount of change with which the pulse waves can be detected (step S205). As a result of comparison, if the calculated amount of change meets the predetermined amount of change, it is determined that a pressure condition within the air bag for detecting the pulse waves is satisfied (YES in step S206). If not, the processes in steps S205 and S206 are repeated until the pressure condition within the air bag is satisfied.

When the pressure condition in the air bag is satisfied (YES in step S206), pressure pump 202 is adjusted such that the pressing level by air bag 250 against the semiconductor pressure sensors becomes an optimal level for detection of the pulse waves (step S207).

With air bag 250 adjusted to the optimal pressure, the pressure information output from the semiconductor pressure sensor, i.e., the waveform data of the pulse waves of the radial artery, is transferred via multiplexer 207 and A/D converter 208 to CPU 209 (step S208).

CPU 209 receives the waveform data, and detects the pulse waves based on the received waveform data. The process of transferring the pulse wave data in step S208 is repeated until it is determined that the waveform data has been received and a prescribed condition for ending the pulse wave detection is satisfied. The process of detecting the pulse waves based on the received waveform data is carried out in a known manner, and thus, detailed description thereof will not be provided here.

If the prescribed condition to end the pulse wave detection is satisfied (YES in step S209), CPU 209 controls valve 204 and drives negative pressure pump 203 (step S210). This releases the pressed-state of semiconductor chip 236 against the wrist, and the series of pulse wave detecting processes are completed.

CPU 209 externally outputs the detected pulse wave information via display portion 213 or the like. Further, the pulse wave information may be used for calculation of an AI (Augmentation Index) to output the AI.

Figure 21:
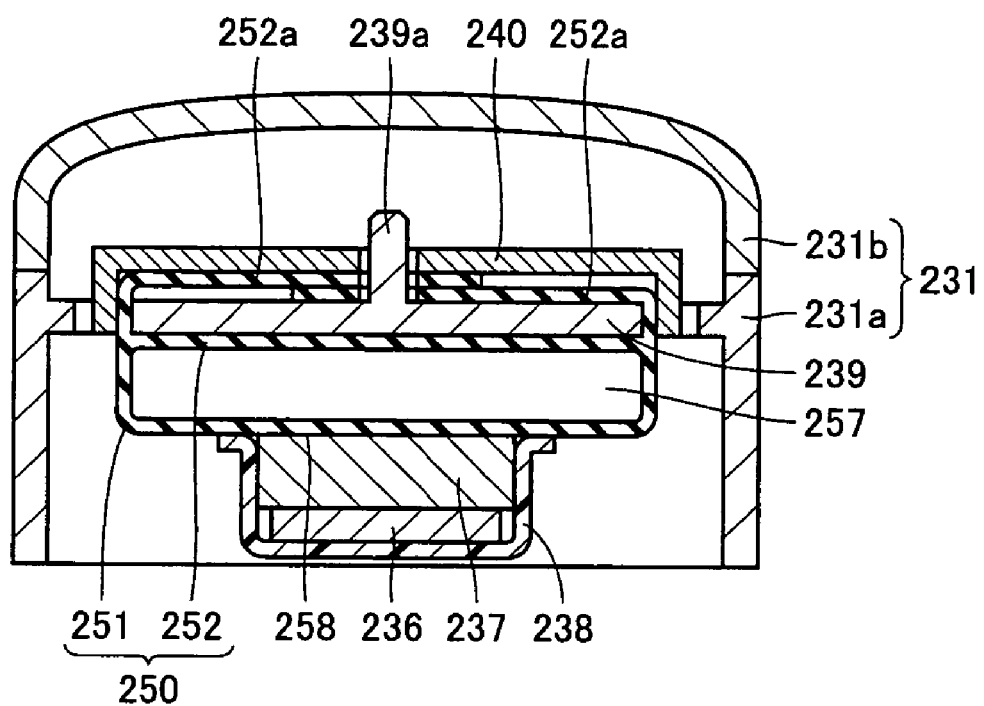
FIG. 21 is a cross sectional view of a case member of the sensor unit of the pulse wave detector according to the second embodiment of the present invention.
Figure 22:
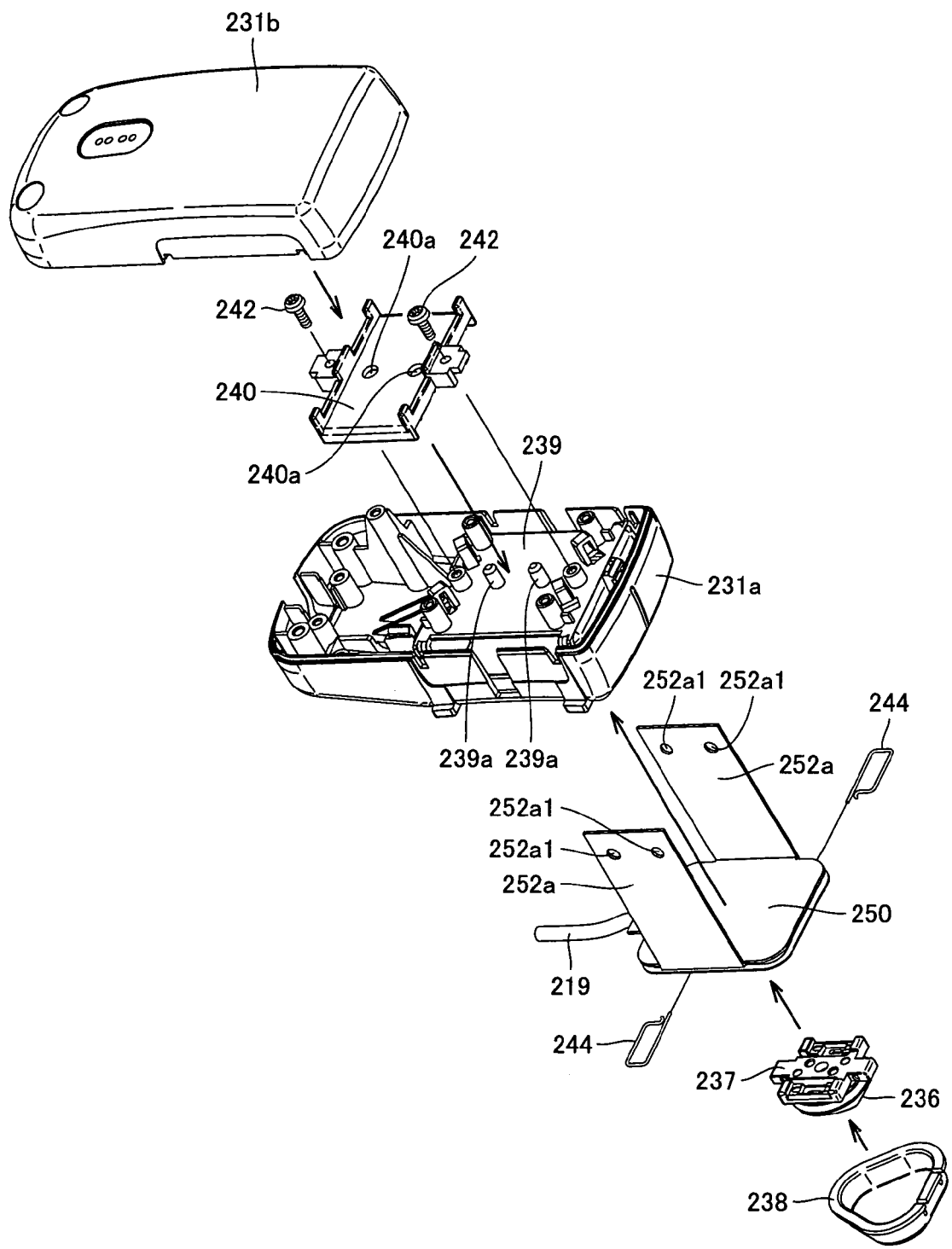
FIG. 22 is a schematic exploded diagram of the case member shown in FIG. 21.
Figure 23:
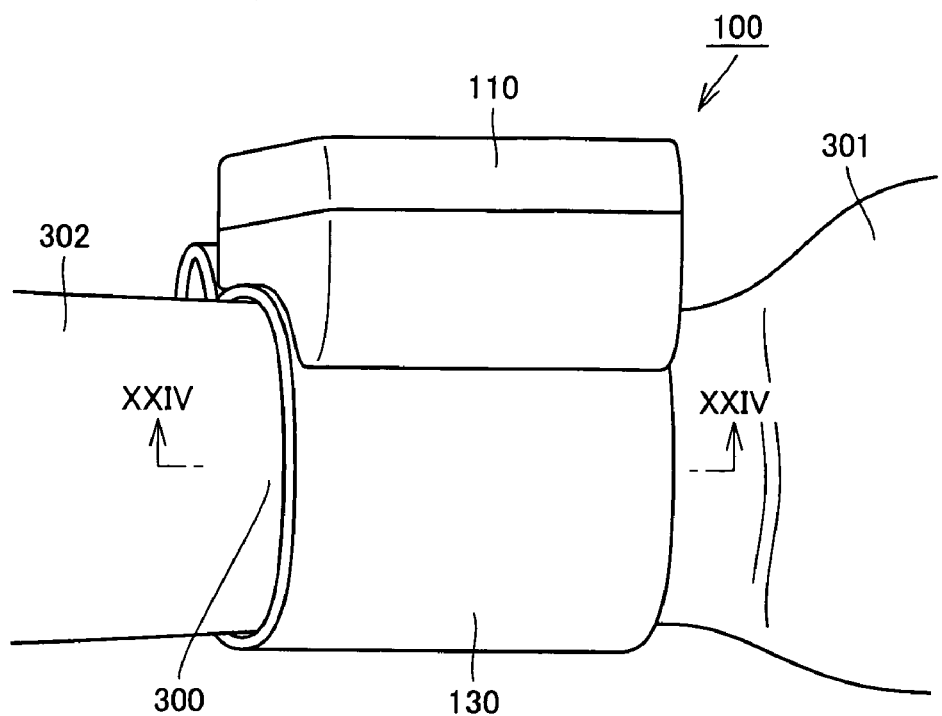
FIG. 23 is a schematic diagram showing the state where a typical wrist blood pressure monitor is mounted on a measurement site of the wrist.
Figure 24:
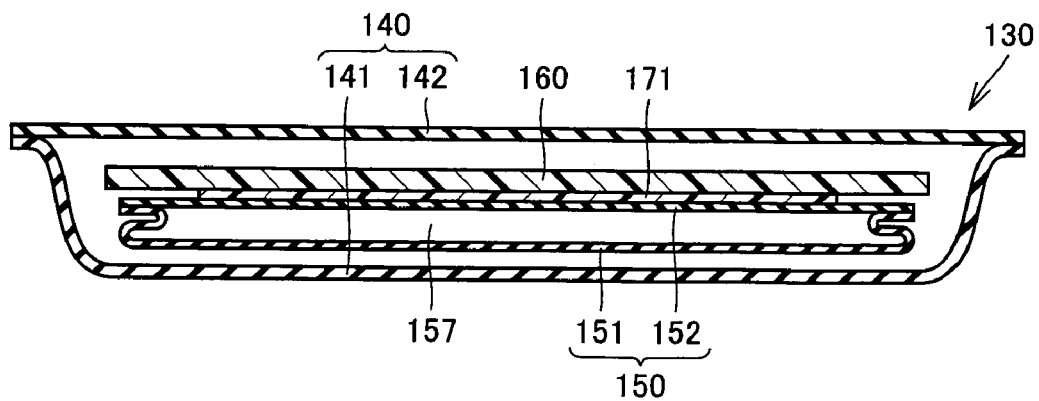
FIG. 24 is a schematic cross sectional view of the cuff for the blood pressure monitor shown in FIG. 23, taken along the line XXIV-XXIV in FIG. 23.
Figure 25:
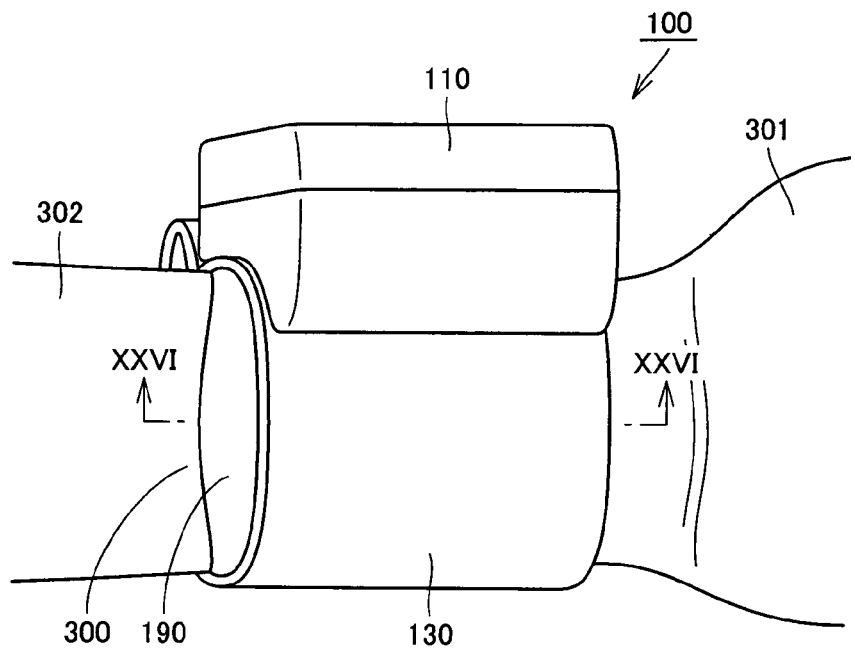
FIG. 25 is a schematic diagram showing the state where there occurs lateral displacement in the cuff for the wrist blood pressure monitor in the measurement state shown in FIG. 23.

FIG. 21 is a cross sectional view of the case member of the sensor unit of the pulse wave detector according to the present embodiment. FIG. 22 is a schematic exploded diagram of the case member shown in FIG. 21. As shown in FIGS. 21 and 22, case member 231 of sensor unit 230 of pulse wave detector 200 according to the present embodiment has a lower case 231a and an upper case 231b. Lower case 231a has a base portion 239 formed in a plate shape, and air bag 250 is secured to this base portion 239. Air bag 250 has a lower wall portion 251 including a working face 258 for pressing the wrist, and an upper wall portion 252 opposite to lower wall portion 251, and has an inflated/deflated space 257 therein. On working face 258 of air bag 250 for pressing the wrist, a support base 237 is attached via a pin 244. Semiconductor chip 236 is secured to the lower surface of support base 237, and is covered by a protective cap 238.

Engagement portions 252a are provided at the respective side end portions of air bag 250. Engagement portions 252a are each folded along the end face of base portion 239 of lower case 231a, and extended onto a second main surface (upper surface) of base portion 239 that is located opposite to a first main surface (lower surface) of base portion 239 facing air bag 250. A hole 252a1 is provided at a prescribed position of engagement portion 252a, and hole 252a1 is hooked onto a hook 239a erected on the upper surface of base portion 239. Further, a plate 240 is attached, from above, to the upper surface of base portion 239 to which engagement portion 252a is engaged. Plate 240 is secured to base portion 239 via a screw 242, so that engagement portion 252a is pressed and secured to the upper surface of base portion 239 in an immovable manner. It is noted that plate 240 has a hole 240a through which hook 239a is passed.

In the above-described pulse wave detector as well, a configuration provided with an air bag that is unlikely to cause lateral displacement can be implemented, as in the case of the blood pressure monitor according to the first embodiment. Thus, it is possible to provide a pulse wave detector that prevents occurrence of lateral displacement and that can press a pressure-sensitive surface against the living body in a stable manner, in the case where the air bag is inflated and the semiconductor sensor is moved downward by a prescribed amount to be pressed against the living body for measurement of pulse waves. Accordingly, a highly reliable, high-precision pulse wave detector can be obtained.

In both of the first and second embodiments described above, explanation was made about the case where the engagement portion is folded back and secured in an immovable manner to the second main surface of the base portion (the outer peripheral surface of the curled elastic member in the case of the cuff for a blood pressure monitor). The configuration however is not restricted thereto. For example, the engagement portion may be secured to a constituent element other than the base portion, or it may be secured to the end face of the base portion if the base portion is sufficiently large in the thickness direction. In any case, the objective of the present invention to prevent lateral displacement can be achieved as long as the engagement portion is folded toward the side of the base portion with respect to an interface portion between the air bag and the base portion, and that the engagement portion is secured in an immovable manner to any place in a region on the side of the base portion with respect to the relevant interface portion.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A cuff for a blood pressure monitor, comprising:
a fluid bag inflated and deflated as a fluid comes in and out;
a cover member containing said fluid bag; and
an elastic member wound annularly around an outer side of said fluid bag and changeable in size in a radial direction; wherein
said fluid bag has an inner wall portion located on an inner side when wound around a living body, an outer wall portion located on an outer side than said inner wall portion, and an engagement portion extending from a side end portion in a width direction of said fluid bag,
said engagement portion is folded at said side end portion toward said elastic member, and secured in an immovable manner to a position on the side of said elastic member with respect to an outer surface of said outer wall portion, and
said engagement portion is provided at least at one place in each side end portion in the width direction of said fluid bag.

2. The cuff for a blood pressure monitor according to claim 1, wherein said engagement portion is located approximately at a central portion in a longitudinal direction of said fluid bag.

3. A cuff for a blood pressure monitor, comprising:
a fluid bag inflated and deflated as a fluid comes in and out;
a cover member containing said fluid bag; and an elastic member wound annularly around an outer side of said fluid bag and changeable in size in a radial direction; wherein said fluid bag has an inner wall portion located on an inner side when wound around a living body, an outer wall portion located on an outer side than said inner wall portion, and an engagement portion extending from a side end portion in a width direction of said fluid bag, said engagement portion is folded at said side end portion toward said elastic member, and secured in an immovable manner to a position on the side of said elastic member with respect to an outer surface of said outer wall portion, said elastic member is formed of a plate-shaped member having an inner peripheral surface facing said fluid bag and an outer peripheral surface opposite to said inner peripheral surface, and said engagement portion is folded at said side end portion onto said outer peripheral surface of said elastic member and disposed on said outer peripheral surface in an immovable manner.

4. The cuff for a blood pressure monitor according to claim 3, wherein said engagement portion is secured directly to the outer peripheral surface of said elastic member.

5. The cuff for a blood pressure monitor according to claim 3, wherein the respective side end portions of said engagement portion are overlapped and secured to each other on said outer peripheral surface.

6. A cuff for a blood pressure monitor, comprising:
a fluid bag inflated and deflated as a fluid comes in and out;
a cover member containing said fluid bag; and
an elastic member wound annularly around an outer side of said fluid bag and changeable in size in a radial direction; wherein said fluid bag has an inner wall portion located on an inner side when wound around a living body, an outer wall portion located on an outer side than said inner wall portion, and an engagement portion extending from a side end portion in a width direction of said fluid bag, said engagement portion is folded at said side end portion toward said elastic member, and secured in an immovable manner to a position on the side of said elastic member with respect to an outer surface of said outer wall portion, said fluid bag is formed by laying a plurality of sheets one on another and joining their rims so that a space is formed therein, and said engagement portion is formed by extending a rim of at least one of said sheets outwards.

7. A blood pressure monitor, comprising:
a cuff for a blood pressure monitor including a fluid bag inflated and deflated as a fluid comes in and out, and an elastic member wound annularly around an outer side of said fluid bag and changeable in size in a radial direction;
an inflating/deflating portion for inflating and deflating said fluid bag;
a pressure detecting portion for detecting a pressure in said fluid bag; and
a blood pressure value calculating portion for calculating a blood pressure value based on pressure information detected by said pressure detecting portion; wherein said fluid bag has an inner wall portion located on an inner side when wound around a living body, an outer wall portion located on an outer side than said inner wall portion, and an engagement portion extending from a side end portion in a width direction of said fluid bag, said engagement portion is folded at said side end portion toward said elastic member, and secured in an immovable manner to a position on the side of said elastic member with respect to an outer surface of said outer wall portion, and said engagement portion is provided at least at one place in each side end portion in the width direction of said fluid bag.

8. A blood pressure monitor, comprising:
a cuff for a blood pressure monitor including a fluid bag inflated and deflated as a fluid comes in and out, a cover member containing said fluid bag, and an elastic member wound annularly around an outer side of said fluid bag and changeable in size in a radial direction, wherein said fluid bag has an inner wall portion located on an inner side when wound around a living body, an outer wall portion located on an outer side than said inner wall portion, and an engagement portion extending from a side end portion in a width direction of said fluid bag, said engagement portion is folded at said side end portion toward said elastic member, and secured in an immovable manner to a position on the side of said elastic member with respect to an outer surface of said outer wall portion, said elastic member is formed of a plate-shaped member having an inner peripheral surface facing said fluid bag and an outer peripheral surface opposite to said inner peripheral surface, and said engagement portion is folded at said side end portion onto said outer peripheral surface of said elastic member and disposed on said outer peripheral surface in an immovable manner.

9. A blood pressure monitor, comprising:
a cuff for a blood pressure monitor including a fluid bag inflated and deflated as a fluid comes in and out, a cover member containing said fluid bag, and an elastic member wound annularly around an outer side of said fluid bag and changeable in size in a radial direction, wherein said fluid bag has an inner wall portion located on an inner side when wound around a living body, an outer wall portion located on an outer side than said inner wall portion, and an engagement portion extending from a side end portion in a width direction of said fluid bag, said engagement portion is folded at said side end portion toward said elastic member, and secured in an immovable manner to a position on the side of said elastic member with respect to an outer surface of said outer wall portion, said fluid bag is formed by laying a plurality of sheets one on another and joining their rims so that a space is formed therein, and said engagement portion is formed by extending a rim of at least one of said sheets outwards.

* * * * *